(12) United States Patent
Padmanabhan

(10) Patent No.: US 10,772,847 B1
(45) Date of Patent: Sep. 15, 2020

(54) COMBINATIONAL FENDILINE FORMULATIONS AND USES THEREOF

(71) Applicant: Jaya Padmanabhan, Tampa, FL (US)

(72) Inventor: Jaya Padmanabhan, Tampa, FL (US)

(73) Assignee: UNIVERSITY OF SOUTH FLORIDA, Tampa, FL (US)

(*) Notice: Subject to any disclaimer, the term of this patent is extended or adjusted under 35 U.S.C. 154(b) by 113 days.

(21) Appl. No.: 15/437,052

(22) Filed: Feb. 20, 2017

Related U.S. Application Data

(60) Provisional application No. 62/296,668, filed on Feb. 18, 2016.

(51) Int. Cl.
| | | |
|---|---|---|
| *A61K 31/137* | (2006.01) |
| *A61K 31/407* | (2006.01) |
| *A61P 35/00* | (2006.01) |
| *A61K 31/55* | (2006.01) |
| *A61K 31/409* | (2006.01) |

(52) U.S. Cl.
CPC .......... *A61K 31/137* (2013.01); *A61K 31/407* (2013.01); *A61K 31/409* (2013.01); *A61K 31/55* (2013.01); *A61P 35/00* (2018.01)

(58) Field of Classification Search
CPC ...... A61K 31/137; A61K 31/407; A61P 35/00
See application file for complete search history.

(56) References Cited

U.S. PATENT DOCUMENTS 6,268,377 B1 * 7/2001 Waldstreicher ...... A61K 31/435
514/10.2

2013/0123286 A1 * 5/2013 Hu .............. C07D 491/04
514/267
2013/0296438 A1 * 11/2013 Hancock ............ G01N 33/5011
514/648

OTHER PUBLICATIONS

Tomizawa et al. (Oncology Letters, 2015, 10, 1468-1472).*
Daughton et al. (Science of the Total Environment, 2013, 443, 324-337).*
Woods et al. (Oncotarget, 6, 35931; Sep. 30, 2015; NPL document 49 of IDS filed Dec. 11, 2017) (Year: 2015).*
Van der Hoeven (Molecular and Cellular Biology, 2013, 33, 237-251) (Year: 2013).*
Kim (Mol Cancer Ther; 10, 1993-9, 2011) (Year: 2011).*
Le WD, Xie WJ, Kong R, Appel SH (1997) Beta-amyloid-induced neurotoxicity of a hybrid septal cell line associated with increased tau phosphorylation and expression of beta-amyloid precursor protein. Journal of neurochemistry 69:978-985.
Lee MS, Kao SC, Lemere CA, Xia W, Tseng HC, Zhou Y, Neve R, Ahlijanian MK, Tsai LH (2003) APP processing is regulated by cytoplasmic phosphorylation. The Journal of cell biology 163:83-95.
Lesne S, Koh MT, Kotilinek L, Kayed R, Glabe CG, Yang A, Gallagher M, Ashe KH (2006) A specific amyloid-beta protein assembly in the brain impairs memory. Nature 440:352-357.

(Continued)

*Primary Examiner* — Theodore R. West
(74) *Attorney, Agent, or Firm* — Thomas | Horstemeyer, LLP

(57) ABSTRACT

Provided herein are formulations that can be effective to kill a pancreatic cancer cell that can include fendiline and a MET inhibitor, an aurora-ABC inhibitor, or an autophagy inhibitor. Also provided herein are methods of treating pancreatic cancer or a symptom thereof in a subject in need thereof, where the method can include the step of administering fendiline and a MET inhibitor, an aurora-ABC inhibitor, or an autophagy inhibitor.

6 Claims, 21 Drawing Sheets

(56) References Cited

OTHER PUBLICATIONS

Levy-Lahad E, Wasco W, Poorkaj P, Romano DM, Oshima J, Pettingell WH, Yu CE, Jondro PD, Schmidt SD, Wang K, et al. (1995) Candidate gene for the chromosome 1 familial Alzheimer's disease locus. Science 269:973-977.
Lin YT, Cheng JT, Liang LC, Ko CY, Lo YK, Lu PJ (2007) the binding and phosphorylation of Thr231 is critical for Tau's hyperphosphorylation and functional regulation by glycogen synthase kinase 3beta. Journal of neurochemistry 103:802-813.
Lopez-Toledano MA, Shelanski ML (2004) Neurogenic effect of beta-amyloid stem cells. The Journal of neuroscience : the official journal of the Society peptide in the development of neural for Neuroscience 24:5439-5444.
Lorenzo A, Yuan M, Zhang Z, Paganetti PA, Sturchler-Pierrat C, Staufenbiel M, Mautino J, Vigo FS, Sommer B, Yankner BA (2000) Amyloid beta interacts with the amyloid precursor protein: a potential toxic mechanism in Alzheimer's disease. Nature neuroscience 3:460-464.
Lovestone S, Reynolds CH, Latimer D, Davis DR, Anderton BH, Gallo JM, Hanger D, Mulot S, Marquardt B, Stabel S, et al. (1994) Alzheimer's disease-like phosphorylation of the microtubule-associated protein tau by glycogen synthase kinase-3 in transfected mammalian cells. Current biology : CB 4:1077-1086.
Lu Q, Soria JP, Wood JG (1993) p44mpk MAP kinase induces Alzheimer type alterations in tau function and in primary hippocampal neurons. Journal of neuroscience research 35:439-4-44.
Majd S, Zarifkar A, Rastegar K, Takhshid MA (2008) Different fibrillar Abeta 1-42 concentrations induce adult hippocampal neurons to reenter various phases of the cell cycle. Brain Res 1218:224-229.
Masters CL, Multhaup G, Simms G, Pottgiesser J, Martins RN, Beyreuther K (1985) Neuronal origin of a cerebral amyloid: neurofibrillary tangles of Alzheimer's disease contain the same protein as the amyloid of plaque cores and blood vessels. The EMBO journal 4:2757-2763.
Mattila PM, Rinne JO, Helenius H, Roytta M (1999) Neuritic degeneration in the hippocampus and amygdala in Parkinson's disease in relation to Alzheimer pathology. Acta neuropathologica 98:157-164.
McShea A, Zelasko DA, Gerst JL, Smith MA (1999) Signal transduction abnormalities in Alzheimer's disease: evidence of a pathogenic stimuli. Brain Res 815:237-242.
Mora N, Santa Barbara Ruiz P, Ferreira N, Serras F (2013) Ras signal triggers beta-amyloid precursor protein (APP) expression. Small GTPases 4:171-173.
Muresan V, Muresan Z (2009) Is abnormal axonal transport a cause, a contributing factor or a consequence of the neuronal pathology in Alzheimer's disease? Future neurology 4:761-773.
Muresan Z, Muresan V (2005) Coordinated transport of phosphorylated amyloid-beta precursor protein and c-Jun NH2-terminal kinase-interacting protein-1. The Journal of cell biology 171:615-625.
Nagy Z, Esiri MM, Smith AD (1997) Expression of cell division markers in the hippocampus in Alzheimer's disease and other neurodegenerative conditions. Acta neuropathologica 93:294-300.
Nicholson AM, Ferreira A (2009) Increased membrane cholesterol might render mature hippocampal neurons more susceptible to beta-amyloid-induced calpain activation and tau toxicity. The Journal of neuroscience : the official journal of the Society for Neuroscience 29:4640-4651.
Nizzari M, Thellung S, Corsaro A, Villa V, Pagano A, Porcile C, Russo C, Florio T (2012) Neurodegeneration in Alzheimer disease: role of amyloid precursor protein and presenilin 1 intracellular signaling. Journal of toxicology 2012:187297.
Nizzari M, Venezia V, Repetto E, Caorsi V, Magrassi R, Gagliani MC, Carlo P, Florio T, Schettini G, Tacchetti C, Russo T, Diaspro A, Russo C (2007) Amyloid precursor protein and Presenilin1 interact with the adaptor GRB2 and modulate ERK 1,2 signaling. The Journal of biological chemistry 282:13833-13844.

Jei JJ, Braak H, An WL, Winblad B, Cowburn RF, Iqbal K, Grundke-Iqbal I (2002) Up-regulation of mitogen-activated Protein kinases ERK1/2 and MEK1/2 is associated with the progression of neurofibrillary degeneration in Alzheimer's Disease. Brain research Molecular brain research 109:45-55.
Porras A, Alvarez AM, Valladares A, Benito M (1998) p42/p44 mitogen-activated protein kinases activation is required for the insulin-like growth factor-I/insulin induced proliferation, but inhibits differentiation, in rat fetal brown adipocytes. Molecular endocrinology 12:825-834.
Prior IA, Hancock JF (2012) Ras trafficking, localization and compartmentalized signalling. Seminars in cell & developmental biology 23:145-153.
Raghunandan R, Ingram VM (1995) Hyperphosphorylation of the cytoskeletal protein Tau by the MAP-kinase PK40erk2: regulation by prior phosphorylation with cAMP-dependent protein kinase A. Biochemical and biophysical research communications 215:1056-1066.
Raina AK, Monteiro MJ, McShea A, Smith MA (1999) The role of cell cycle-mediated events in Alzheimer's disease. International journal of experimental pathology 80:71-76.
Rapoport M, Ferreira A (2000) PD98059 prevents neurite degeneration induced by fibrillar beta-amyloid in mature hippocampal neurons. Journal of neurochemistry 74:125-133.
Reifert J, Hartung-Cranston D, Feinstein SC (2011) Amyloid beta-mediated cell death of cultured hippocampal neurons reveals extensive Tau fragmentation without increased full-length tau phosphorylation. The Journal of biological chemistry 286:20797-20811.
Reynolds CH, Utton MA, Gibb GM, Yates A, Anderton BH (1997) Stress-activated protein kinase/c-jun N-terminal kinase phosphorylates tau protein. Journal of neurochemistry 68:1736-1744.
Reynolds CH, Betts JC, Blackstock WP, Nebreda AR, Anderton BH (2000) Phosphorylation sites on tau identified by nanoelectrospray mass spectrometry: differences in vitro between the mitogen-activated protein kinases ERK2, c-Jun N-terminal kinase and P38, and glycogen synthase kinase-3beta. Journal of neurochemistry 74:1587-1595.
Rogaev EI, Sherrington R, Rogaeva EA, Levesque G, Ikeda M, Liang Y, Chi H, Lin C, Holman K, Tsuda T, et al. (1995) Familial Alzheimer's disease in kindreds with missense mutations in a gene on chromosome 1 related to the Alzheimers disease type 3 gene. Nature 376:775-778.
Rojas JM, Oliva JL, Santos E (2011) Mammalian son of sevenless Guanine nucleotide exchange factors: old concepts and new perspectives. Genes & cancer 2:298-305.
Ryan KA, Pimplikar SW (2005) Activation of GSK-3 and phosphorylation of CRMP2 in transgenic mice expressing APP intracellular domain. The Journal of cell biology 171:327-335.
Shaked GM, Kummer MP, Lu DC, Galvan V, Bredesen DE, Koo EH (2006) Abeta induces cell death by direct interaction with its cognate extracellular domain on APP (APP 597-624). FASEB journal : official publication of the Federation of American Societies for Experimental Biology 20:1254-1256.
Shankar GM, Li S, Mehta TH, Garcia-Munoz A, Shepardson NE, Smith I, Brett FM, Farrell MA, Rowan MJ, Lemere CA, Regan CM, Walsh DM, Sabatini BL, Selkoe DJ (2008) Amyloid-beta protein dimers isolated directly from Alzheimer's brains impair synaptic plasticity and memory. Nature medicine 14:837-842.
Sherrington R et al. (1995) Cloning of a gene bearing missense mutations in early-onset familial Alzheimer's disease. Nature 375:754-760.
Sola Vigo F, Kedikian G, Heredia L, Heredia F, Anel AD, Rosa AL, Lorenzo A (2009) Amyloid-beta precursor protein mediates neuronal toxicity of amyloid beta through Go protein activation. Neurobiology of aging 30:1379-1392.
Standen CL, Brownlees J, Grierson AJ, Kesavapany S, Lau KF, McLoughlin DM, Miller CC (2001) Phosphorylation of thr(668) in the cytoplasmic domain of the Alzheimer's disease amyloid precursor protein by stress-activated protein kinase 1b (Jun N-terminal kinase-3). Journal of neurochemistry 76:316-320.

(56) References Cited

OTHER PUBLICATIONS

Suh YH, Checler F (2002) Amyloid precursor protein, presenilins, and alpha-synuclein: molecular pathogenesis and pharmacological applications in Alzheimer's disease. Pharmacological reviews 54:469-525.

Suzuki T, Oishi M, Marshak DR, Czernik AJ, Nairn AC, Greengard P (1994) Cell cycle-dependent regulation of the phosphorylation and metabolism of the Alzheimer amyloid precursor protein. The EMBO journal 13:1114-1122.

Takashima A, Honda T, Yasutake K, Michel G, Murayama O, Murayama M, Ishiguro K, Yamaguchi H (1998) Activation of tau protein kinase 1/glycogen synthase kinase-3beta by amyloid beta peptide (25-35) enhances phosphorylation of tau in hippocampal neurons. Neuroscience research 31:317-323.

Takeuchi H, Mizuno T, Zhang G, Wang J, Kawanokuchi J, Kuno R, Suzumura A (2005) Neuritic beading induced by activated microglia is an early feature of neuronal dysfunction toward neuronal death by inhibition of mitochondrial respiration and axonal transport. The Journal of biological chemistry 280:10444-10454.

Tanaka T, Zhong J, Iqbal K, Trenkner E, Grundke-Iqbal I (1998) The regulation of phosphorylation of tau in SY5Y neuroblastoma cells: the role of protein phosphatases. FEBS letters 426:248-254.

Trojanowski JQ, Mawal-Dewan M, Schmidt ML, Martin J, Lee VM (1993) Localization of the mitogen activated protein kinase ERK2 in Alzheimer's disease neurofibrillary tangles and senile plaque neurites. Brain Res 618:333-337.

Utton MA, Vandecandelaere A, Wagner U, Reynolds CH, Gibb GM, Miller CC, Bayley PM, Anderton BH (1997) Phosphorylation of tau by glycogen synthase kinase 3beta affects the ability of tau to promote microtubule self-assembly. The Biochemical journal 323 (Pt 3):741-747.

Vincent I, Jicha G, Rosado M, Dickson DW (1997) Aberrant expression of mitotic cdc2/cyclin B1 kinase in degenerating neurons of Alzheimer's disease brain. The Journal of neuroscience : the official journal of the Society for Neuroscience 17:3588-3598.

Walsh DM, Selkoe DJ (2004) Oligomers on the brain: the emerging role of soluble protein aggregates in neurodegeneration. Protein and peptide letters 11:213-228.

Wildsmith KR, Holley M, Savage JC, Skerrett R, Landreth GE (2013) Evidence for impaired amyloid beta clearance in Alzheimer's disease. Alzheimer's research & therapy 5:33.

Zhou F, Gong K, Song B, Ma T, van Laar T, Gong Y, Zhang L (2012) The APP intracellular domain (AICD) inhibits Wnt signalling and promotes neurite outgrowth. Biochimica et biophysica acta 1823:1233-1241.

Woods NK, Padmanabhan J. Inhibition of amyloid precursor protein processing enhances gemcitabine-mediated cytotoxicity in pancreatic cancer cells. J Biol Chem. Oct. 18, 2013;288(42):30114-24.

Woods N, Trevino J, Coppola D, Chellappan S, Yang S, Padmanabhan J. Fendiline inhibits proliferation and invasion of pancreatic cancer cells by interfering with ADAM10 activation and β-catenin signaling. Oncotarget. Nov. 2015;6(34):35931-48.

Alcock RA, Dey S, Chendil D, Inayat MS, Mohiuddin M, Hartman G, Chatfield LK, Gallicchio VS, Ahmed MM (2002) Farnesyltransferase inhibitor (L-744,832) restores TGF-beta type II receptor expression and enhances radiation sensitivity in K-ras mutant pancreatic cancer cell line MIA PaCa-2. Oncogene 21:7883-7890.

Aplin AE, Gibb GM, Jacobsen JS, Gallo JM, Anderton BH (1996) In vitro phosphorylation of the cytoplasmic domain of the amyloid precursor protein by glycogen synthase kinase-3beta. Journal of neurochemistry 67:699-707.

Arendt T, Holzer M, Grossmann A, Zedlick D, Bruckner MK (1995) Increased expression and subcellular translocation of the mitogen activated protein kinase kinase and mitogen-activated protein kinase in Alzheimer's disease. Neuroscience 68:5-18.

Baldin V, Lukas J, Marcote MJ, Pagano M, Draetta G (1993) Cyclin D1 is a nuclear protein required for cell cycle progression in G1. Genes & development 7:812-821.

Balmanno K, Cook SJ (1999) Sustained MAP kinase activation is required for the expression of cyclin D1, p21Cip1 and a subset of AP-1 proteins in CCL39 cells. Oncogene 18:3085-3097.

Barge RM, Dorrestijn J, Falkenburg JH, Willemze R, Maassen JA (1998) Unconventional rapid Erk1,2 activation is indispensable for proliferation of the growth factor-independent myeloid leukemic cell line KG1. Leukemia 12:699-704.

Blanchard BJ, devi Raghunandan R, Roder HM, Ingram VM (1994) Hyperphosphorylation of human TAU by brain kinase PK40erk beyond phosphorylation by cAMP-dependent PKA: relation to Alzheimer's disease. Biochemical and Biophysical research communications 200:187-194.

Braak H, Braak E (1991) Neuropathological stageing of Alzheimer-related changes. Acta neuropathologica 82:239-259.

Braak H, Braak E (1995) Staging of Alzheimer's disease-related neurofibrillary changes. Neurobiology of aging 16:271-278; discussion 278-284.

Busciglio J, Lorenzo A, Yeh J, Yankner BA (1995) beta-amyloid fibrils induce tau phosphorylation and loss of microtubule binding. Neuron 14:879-888.

Busser J, Geldmacher DS, Herrup K (1998) Ectopic cell cycle proteins predict the sites of neuronal cell death in Alzheimer's disease brain. The Journal of neuroscience : the official journal of the Society for Neuroscience 18:2801-2807.

Chang KA, Kim HS, Ha TY, Ha JW, Shin KY, Jeong YH, Lee JP, Park CH, Kim S, Baik TK, Suh YH (2006) Phosphorylation of amyloid precursor protein (APP) at Thr668 regulates the nuclear translocation of the APP intracellular domain and induces neurodegeneration. Molecular and cellular biology 26:4327-4338.

Chaput D, Kirouac LH, Bell-Temin H, Stevens SM, Jr., Padmanabhan J (2012) SILAC-based proteomic analysis to investigate the impact of amyloid precursor protein expression in neuronal-like B103 cells. Electrophoresis 33:3728-3737.

Cho JH, Johnson GV (2003) Glycogen synthase kinase 3beta phosphorylates tau at both primed and unprimed sites. Differential impact on microtubule binding. The Journal of biological chemistry 278:187-193.

Cho JH, Johnson GV (2004) Primed phosphorylation of tau at Thr231 by glycogen synthase kinase 3beta (GSK3beta) plays a critical role in regulating tau's ability to bind and stabilize microtubules. Journal of neurochemistry 88:349-358.

Copani A, Condorelli F, Caruso A, Vancheri C, Sala A, Giuffrida Stella AM, Canonico PL, Nicoletti F, Sortino MA (1999) Mitotic signaling by beta-amyloid causes neuronal death. FASEB journal : official publication of the Federation of American Societies for Experimental Biology 13:2225-2234.

Cosgaya JM, Latasa MJ, Pascual A (1996) Nerve growth factor and ras regulate beta-amyloid precursor protein gene expression in PC12 cells. Journal of neurochemistry 67:98-104.

Dabrowski A, Groblewski GE, Schafer C, Guan KL, Williams JA (1997) Cholecystokinin and EGF activate a MAPK cascade by different mechanisms in rat pancreatic acinar cells. The American journal of physiology 273:C1472-1479.

Delisle MB, Carpenter S (1984) Neurofibrillary axonal swellings and amyotrophic lateral sclerosis. Journal of the neurological sciences 63:241-250.

DeMattos RB, Cirrito JR, Parsadanian M, May PC, O'Dell MA, Taylor JW, Harmony JA, Aronow BJ, Bales KR, Paul SM, Holtzman DM (2004) ApoE and clusterin cooperatively suppress Abeta levels and deposition: evidence that ApoE regulates extracellular Abeta metabolism in vivo. Neuron 41:193-202.

Dickson TC, King CE, McCormack GH, Vickers JC (1999) Neurochemical diversity of dystrophic neurites in the early and late stages of Alzheimer's disease. Experimental neurology 156:100-110.

Dineley KT, Westerman M, Bui D, Bell K, Ashe Kh, Sweatt JD (2001) Beta-amyloid activates the mitogen-activated protein kinase cascade via hippocampal alpha7 nicotinic acetylcholine receptors: in vitro and in vivo mechanisms related to Alzheimer's disease. The Journal of neuroscience : the official journal of the Society for Neuroscience 21:4125-4133.

Drewes G, Lichtenberg-Kraag B, Doring F, Mandelkow EM, Biernat J, Goris J, Doree M, Mandelkow E (1992) Mitogen activated protein

(56) References Cited

OTHER PUBLICATIONS (MAP) kinase transforms tau protein into an Alzheimer-like state. The EMBO journal 11:2131-2138.

Ekinci FJ, Malik KU, Shea TB (1999) Activation of the L voltage-sensitive calcium channel by mitogen-activated protein (MAP) kinase following exposure of neuronal cells to beta-amyloid. MAP kinase mediates beta-amyloid-induced neurodegeneration. The Journal of biological chemistry 274:30322-30327.

Ferrer I, Blanco R, Carmona M, Ribera R, Goutan E, Puig B, Rey MJ, Cardozo A, Vinals F, Ribalta T (2001) Phosphorylated map kinase (ERK1, ERK2) expression is associated with early tau deposition in neurones and glial cells, but not with increased nuclear DNA vulnerability and cell death, in Alzheimer disease, Pick's disease, progressive supranuclear palsy and corticobasal degeneration. Brain pathology 11:144-158.

Gartner U, Holzer M, Arendt T (1999) Elevated expression of p21ras is an early event in Alzheimer's disease and precedes neurofibrillary degeneration. Neuroscience 91:1-5.

Gartner U, Holzer M, Heumann R, Arendt T (1995) Induction of p21ras in Alzheimer pathology. Neuroreport 6:1441-1444.

Geryk-Hall M, Yang Y, Hughes DP (2010) Driven to death: Inhibition of farnesylation increases Ras activity and promotes growth arrest and cell death [corrected]. Mol Cancer Ther 9:1111-1119.

Geula C, Wu CK, Saroff D, Lorenzo A, Yuan M, Yankner BA (1998) Aging renders the brain vulnerable to amyloid beta-protein neurotoxicity. Nature medicine 4:827-831.

Giovanni A, Wirtz-Brugger F, Keramaris E, Slack R, Park DS (1999) Involvement of cell cycle elements, cyclin-dependent kinases, pRb, and E2F x DP, in B-amyloid-induced neuronal death. The Journal of biological chemistry 274:19011-19016.

Glenner GG, Wong CW (1984) Alzheimer's disease and Down's syndrome: sharing of a unique cerebrovascular amyloid fibril protein. Biochemical and biophysical research communications 122:1131-1135.

Goate A, Chartier-Harlin MC, Mullan M, Brown J, Crawford F, Fidani L, Giuffra L, Haynes A, Irving N, James L, et al. (1991) Segregation of a missense mutation in the amyloid precursor protein gene with familial Alzheimer's disease. Nature 349:704-706.

Goedert M, Cohen ES, Jakes R, Cohen P (1992) p42 MAP kinase phosphorylation sites in microtubule-associated protein tau are dephosphorylated by protein phosphatase 2A1. Implications for Alzheimer's disease [corrected]. FEBS letters 312:95-99.

Goedert M, Jakes R, Crowther RA, Cohen P, Vanmechelen E, Vandermeeren M, Cras P (1994) Epitope mapping of monoclonal antibodies to the paired helical filaments of Alzheimer's disease: identification of phosphorylation sites in tau protein. The Biochemical journal 301 ( Pt 3):871-877.

Gold G, Bouras C, Kovari E, Canuto A, Glaria BG, Malky A, Hof PR, Michel JP, Giannakopoulos P (2000) Clinical validity of Braak neuropathological staging in the oldest-old. Acta neuropathologica 99:579-582; discussion 583-574.

Gotz J, Chen F, van Dorpe J, Nitsch RM (2001) Formation of neurofibrillary tangles in P301l tau transgenic mice induced by Abeta 42 fibrils. Science 293:1491-1495.

Hanger DP, Hughes K, Woodgett JR, Brion JP, Anderton BH (1992) Glycogen synthase kinase-3 induces Alzheimer's dlisease-like phosphorylation of tau: generation of paired helical filament epitopes and neuronal localisation of the kinase. Neuroscience letters 147:58-62.

Hardy J (1997) Amyloid, the presenilins and Alzheimer's disease. Trends in neurosciences 20:154-159.

Hyman BT, Elvhage TE, Reiter J (1994) Extracellular signal regulated kinases. Localization of protein and mRNA in the human hippocampal formation in Alzheimer's disease. The American journal of pathology 144:565-572.

Iijima K, Ando K, Takeda S, Satoh Y, Seki T, Itohara S, Greengard P, Kirino Y, Nairn AC, Suzuki T (2000) Neuron-specific phosphorylation of Alzheimer's beta-amyloid precursor protein by cyclin-dependent kinase 5. Journal of neurochemistry 75:1085-1091.

Iversen L, Tu HL, Lin WC, Christensen SM, Abel SM, Iwig J, Wu HJ, Gureasko J, Rhodes C, Petit RS, Hansen SD, Thill P, Yu CH, Stamou D, Chakraborty AK, Kuriyan J, Groves JT (2014) Molecular kinetics. Ras activation by SOS: allosteric regulation by altered fluctuation dynamics. Science 345:50-54.

Jaaro H, Rubinfeld H, Hanoch T, Seger R (1997) Nuclear translocation of mitogen-activated protein kinase kinase (MEK1) in response to mitogenic stimulation. Proceedings of the National Academy of Sciences of the United States of America 94:3742-3747.

Jin LW, Ninomiya H, Roch JM, Schubert D, Masliah E, Otero DA, Saitoh T (1994) Peptides containing the RERMS sequence of amyloid beta/A4 protein precursor bind cell surface and promote neurite extension. The Journal of neuroscience : the official journal of the Society for Neuroscience 14:5461-5470.

Judge M, Hornbeck L, Potter H, Padmanabhan J (2011) Mitosis-specific phosphorylation of amyloid precursor protein at threonine 668 leads to its altered processing and association with centrosomes. Molecular neurodegeneration 6:80. 1-21.

Kayed R, Head E, Thompson JL, McIntire TM, Milton SC, Cotman CW, Glabe CG (2003) Common structure of soluble amyloid oligomers implies common mechanism of pathogenesis. Science 300:486-489.

Kedikian G, Heredia F, Salvador VR, Raimunda D, Isoardi N, Heredia L, Lorenzo A (2010) Secreted amyloid precursor protein and holo-APP bind amyloid beta through distinct domains eliciting different toxic responses on hippocampal neurons. Journal of neuroscience research 88:1795-1803.

Kim J, Basak JM, Holtzman DM (2009) The role of apolipoprotein E in Alzheimer's disease. Neuron 63:287-303.

Klein WL, Krafft GA, Finch CE (2001) Targeting small Abeta oligomers: the solution to an Alzheimer's disease conundrum? Trends in neurosciences 24:219-224.

Kobayashi S, Ishiguro K, Omori A, Takamatsu M, Arioka M, Imahori K, Uchida T (1993) A cdc2-related kinase PSSALRE/cdk5 is homologous with the 30 kDa subunit of tau protein kinase II, a proline-directed protein kinase associated with microtubule. FEBS letters 335:171-175.

Lambert MP, Barlow AK, Chromy BA, Edwards C, Freed R, Liosatos M, Morgan TE, Rozovsky I, Trommer B, Viola KL, Wals P, Zhang C, Finch CE, Krafft GA, Klein WL (1998) Diffusible, nonfibrillar ligands derived from Abeta1-42 are potent central nervous system neurotoxins. Proceedings of the National Academy of Sciences of the United States of America 95:6448-6453.

\* cited by examiner

FIG. 5A
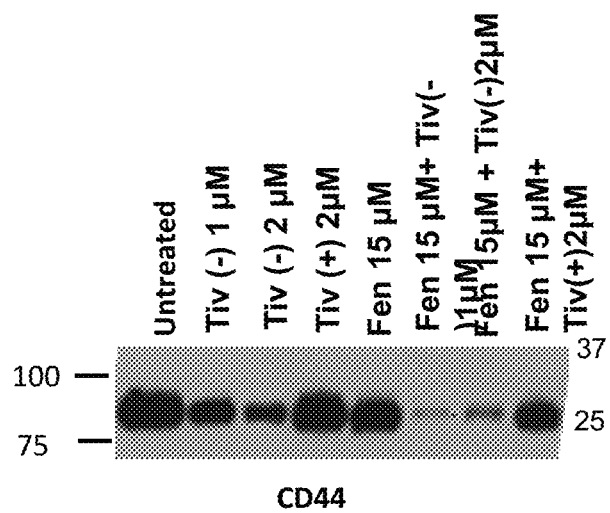
CD44
FIG. 5D
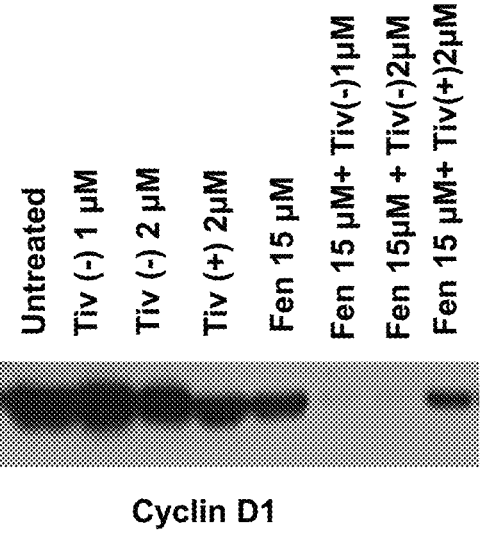
Cyclin D1
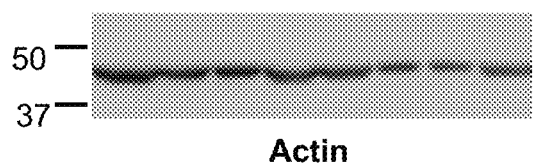
C-myc
Actin
FIG. 5B
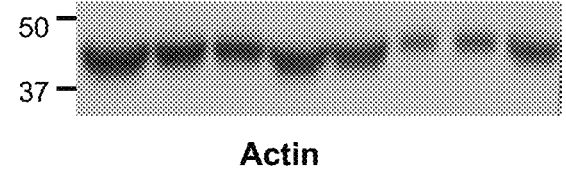
Actin
FIG. 5C
FIG. 5E

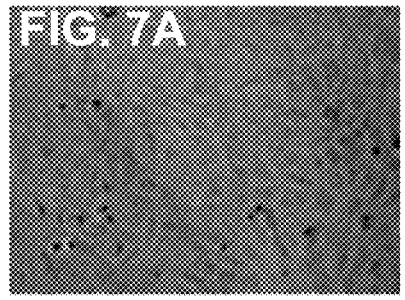
Untreated
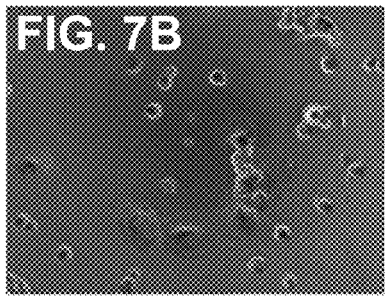
Fendiline 1 μM
Tivantinib (-) 1 μM
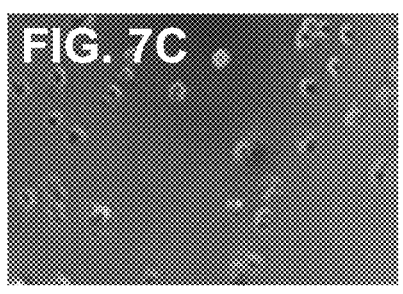
Tivantinib (-) 1 μM
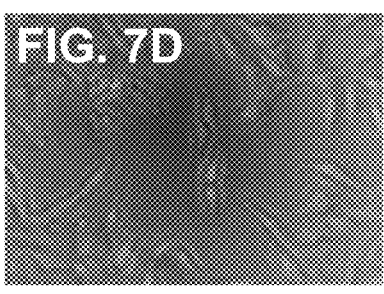
Fendiline 1 μM
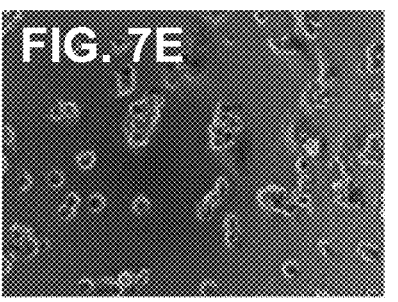
Fendiline 5 μM
Tivantinib (-) 1 μM
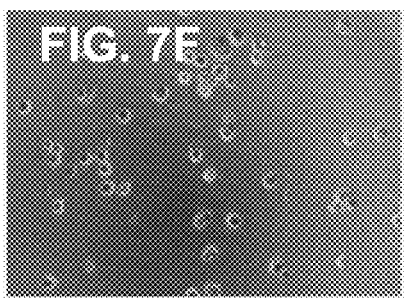
Fendiline 10 μM
Tivantinib (-) 1 μM
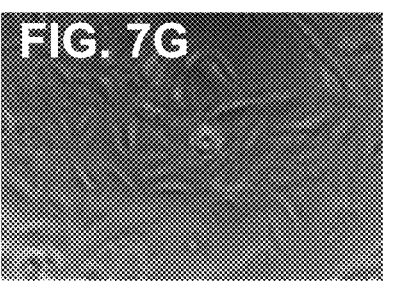
Fendiline 5 μM
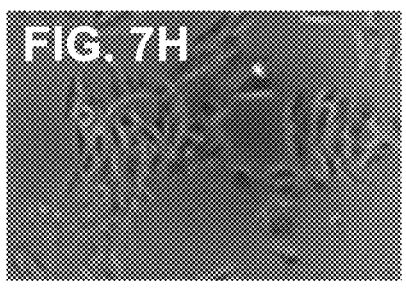
Fendiline 10 μM

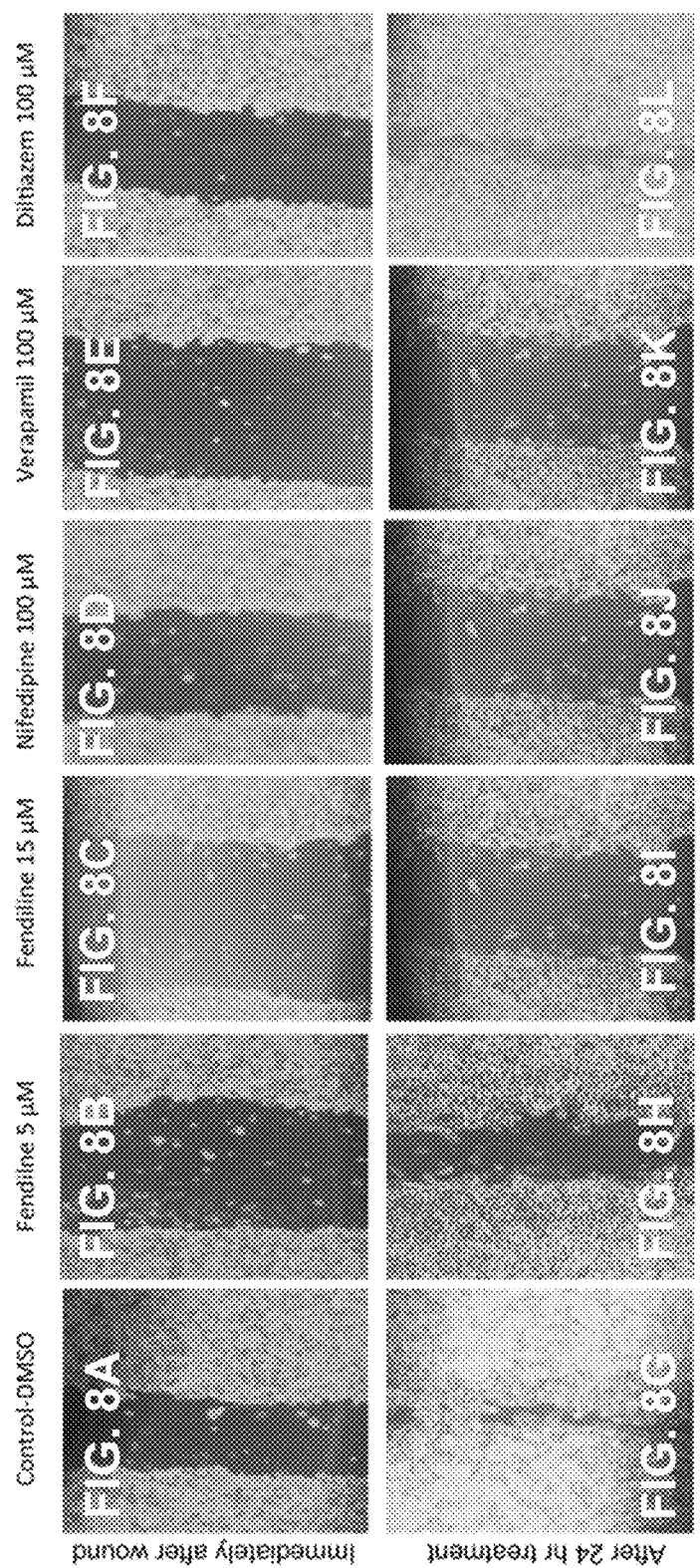

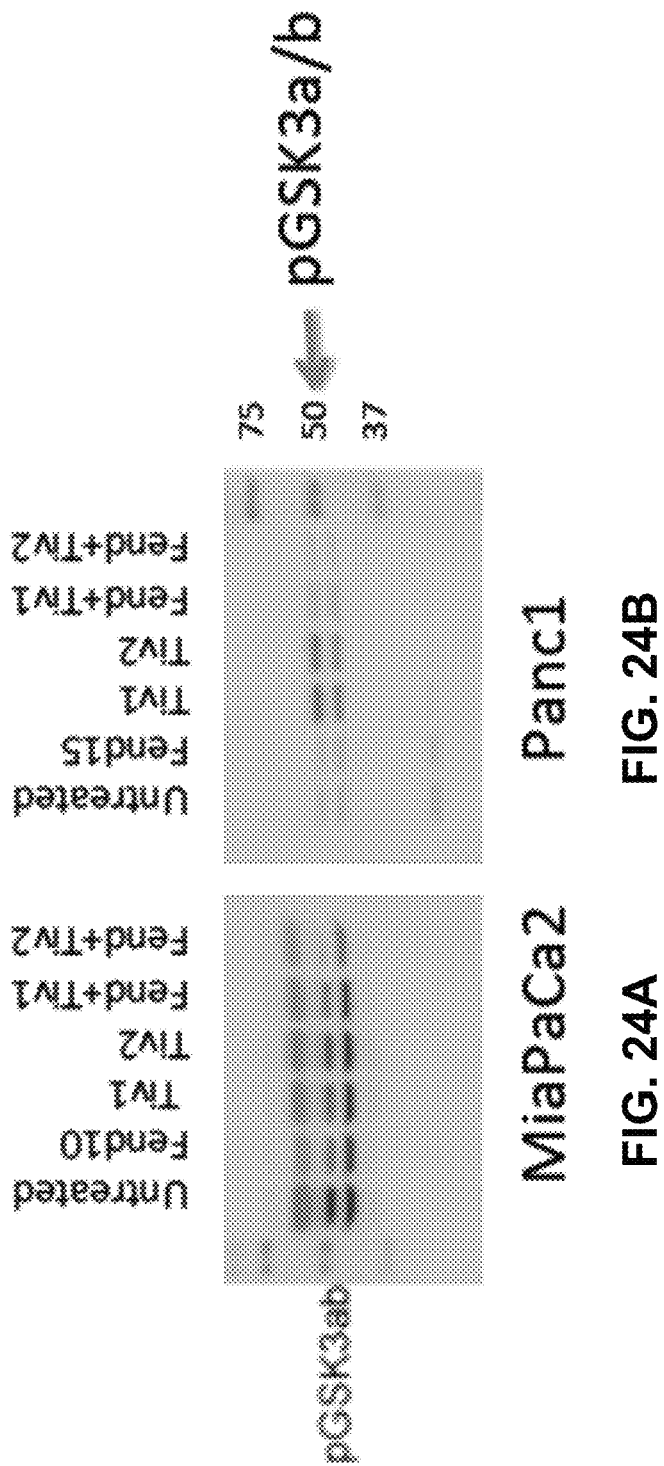

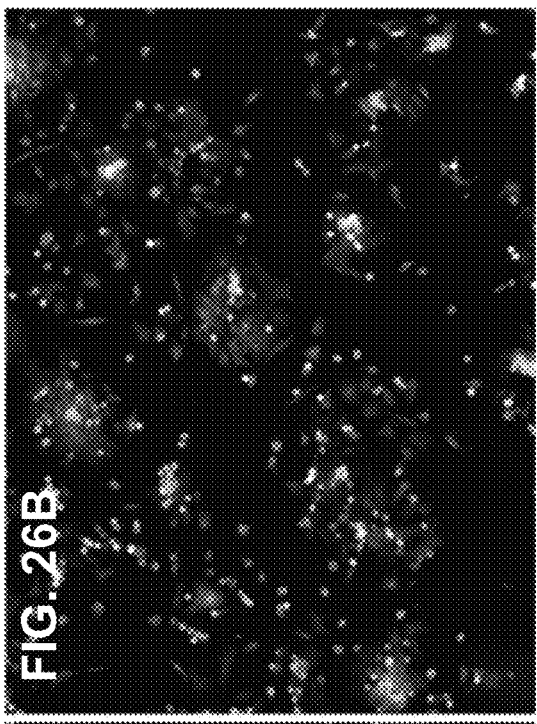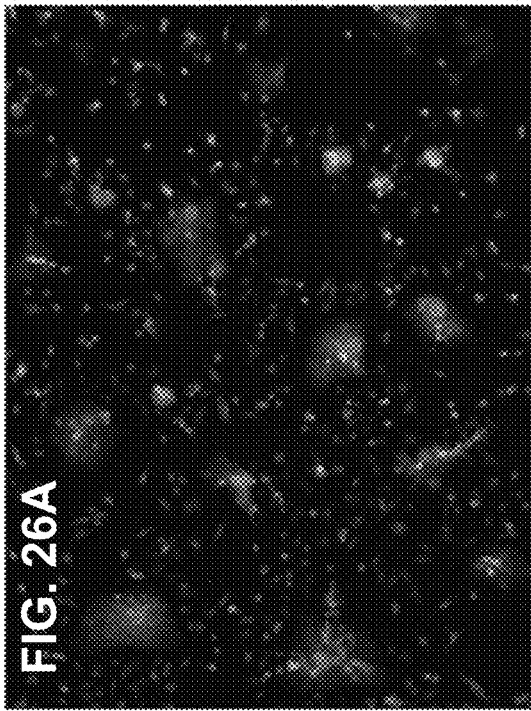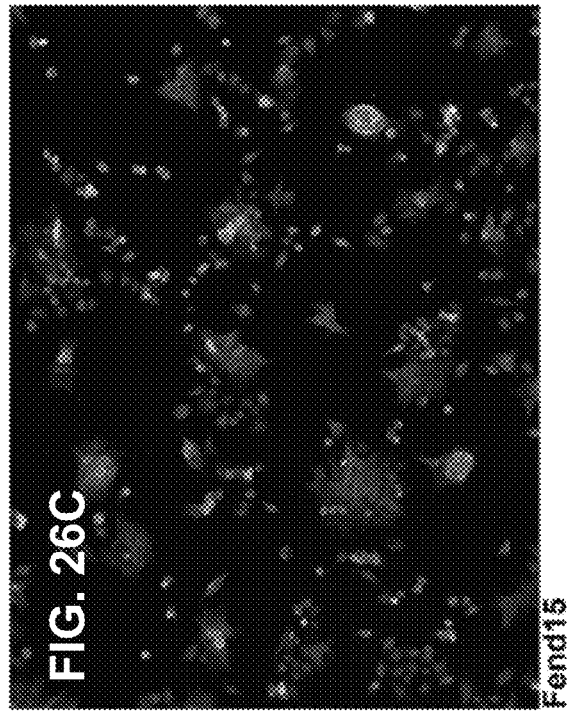

US 10,772,847 B1

COMBINATIONAL FENDILINE FORMULATIONS AND USES THEREOF

CROSS-REFERENCE TO RELATED APPLICATIONS

This application claims the benefit of and priority to U.S. Provisional Patent Application No. 62/296,668, filed on Feb. 18, 2016 entitled "METHOD OF TREATING PANCREATIC CANCER USING COMBINATORIAL TREATMENT WITH FENDILINE," the contents of which is incorporated by reference herein in its entirety.

BACKGROUND

Pancreatic cancer (PC) is one of the deadliest forms of cancer and is the fourth leading cause of death in the United States. PC is often diagnosed at a very late stage when the cancer is aggressive and has metastasized. As such, there exists a need for improved treatments for pancreatic cancer.

SUMMARY

Provided herein are methods of treating pancreatic cancer or a symptom thereof in a subject in need thereof, where the method can include the step of co-administering an effective amount of fendiline and an effective amount of a MET inhibitor, an aurora-ABC inhibitor, or an autophagy inhibitor to the subject in need thereof. The effective amount of fendiline can be a least effective amount. The effective amount of the MET inhibitor, the aurora-ABC inhibitor, or the autophagy inhibitor can be the least effective amount of the MET inhibitor, the aurora-ABC inhibitor, or the autophagy inhibitor. The effective amount of the MET inhibitor, the aurora-ABC inhibitor, or the autophagy inhibitor can be the least effective amount of the MET inhibitor, the aurora-ABC inhibitor, or the autophagy inhibitor. In some embodiments, a MET inhibitor can be co-administered with fendiline during the step of co-administering and wherein the MET inhibitor is tivantinib. In some embodiments, an aurora ABC inhibitor can be co-administered with fendiline during the step of co-administering and wherein the aurora ABC inhibitor can be alisertib. In some embodiments, an autophagy inhibitor can be co-administered with fendiline during the step of co-administering and wherein the autophagy inhibitor can be verteporfin. The pancreatic cancer can be a resistant pancreatic cancer.

Also provided herein are methods of treating pancreatic cancer or a symptom thereof in a subject in need thereof, where the method can include the step of co-administering an effective amount of fendiline and an effective amount of tivantinib to the subject in need thereof. The effective amount of fendiline can be a least effective amount. The effective amount of tivantinib can be a least effective amount. The pancreatic cancer can be a resistant pancreatic cancer.

Also provided herein are formulations that can be effective to kill a pancreatic cancer cell, where the formulation can be composed of an effective amount of fendiline, an effective amount of a MET inhibitor, a an aurora-ABC inhibitor, or an autophagy inhibitor and a pharmaceutically acceptable carrier. In some embodiments, the formulation can include a MET-inhibitor, and wherein the MET-inhibitor can be tivantinib. The effective amount of fendiline can be a least effective amount. The effective amount of tivantinib can be a least effective amount of tivantinib. In some embodiments, the effective amount of the MET inhibitor, the aurora-ABC inhibitor, or the autophagy inhibitor can be a least effective amount of the MET inhibitor, the aurora-ABC inhibitor, or the autophagy inhibitor. In some embodiments, the pancreatic cell is a resistant pancreatic cell.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 4B shows an image of a blot that was reprobed with actin antibody for protein normalization.

FIGS. 5A-5E show images of representative blots that can demonstrate that Tivantinib and Fendiline decreases the expression of (FIG. 5A) CD44, (FIG. 5B) c-myc, and (FIG. 5D) cyclin D1 which are important for cancer cell migration and proliferation. FIGS. 5C and 5E show blots that were reprobed with actin antibody for protein normalization.

FIGS. 7A-7H show microscopic images that can demonstrate cell morphology cell morphology differences, which can be indicative of apoptosis, upon treatment with varying concentrations of fendiline and tivantinib in Panc1 cells.

FIGS. 8A-8L show images of MiaPaCa2 cell treated with various calcium channel blockers. MiaPaCa2 cells were plated to confluency, growth arrested by serum starvation, and scratch wound was made. Cell culture medium with or without different calcium channel blockers at the indicated concentrations was added to the cells and images were taken immediately after the wound was made or after 24 hours.

Panc1 cells were plated to confluency, growth arrested by serum starvation, and scratch wound was made. Cell culture medium with or without fendiline and tivantinib at the indicated concentration was added to the cells and images were taken immediately after the wound was made or after 24 hours.

Figure 11:
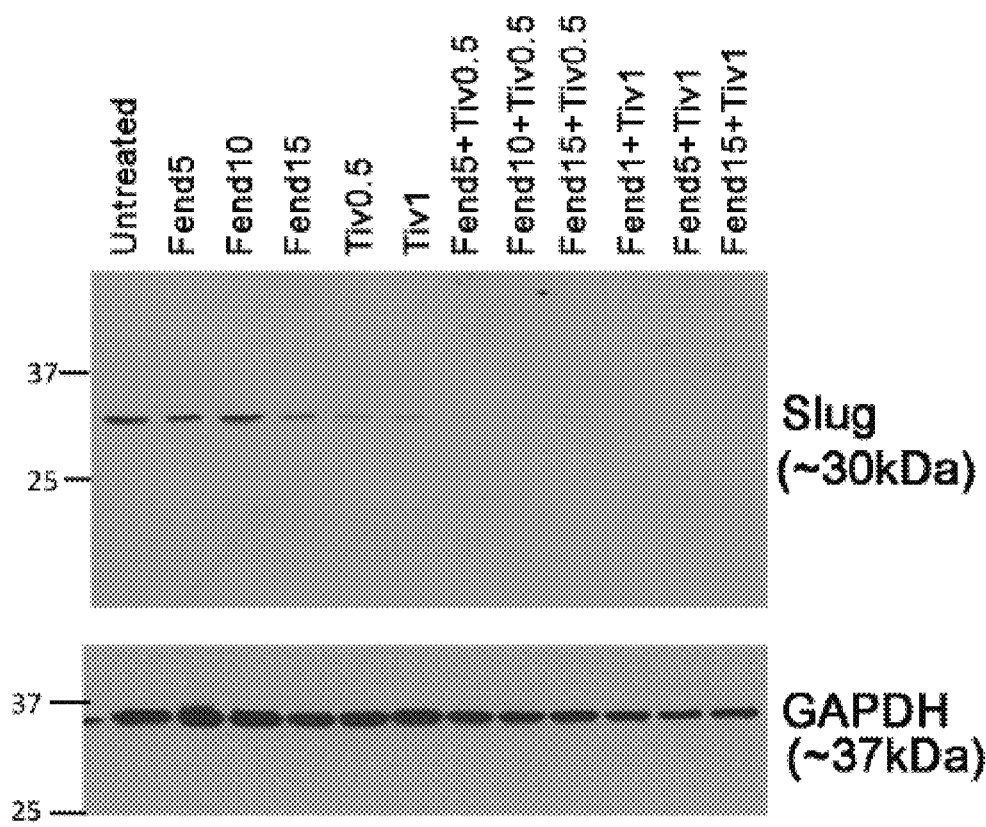

FIG. 11 shows images of representative blots that can demonstrate the effect of co-treatment of fendiline and tivantinib on the expression of Slug, which is a transcriptional repressor that can bind to the integrin promoter and decrease cell adhesion.

Figure 12:
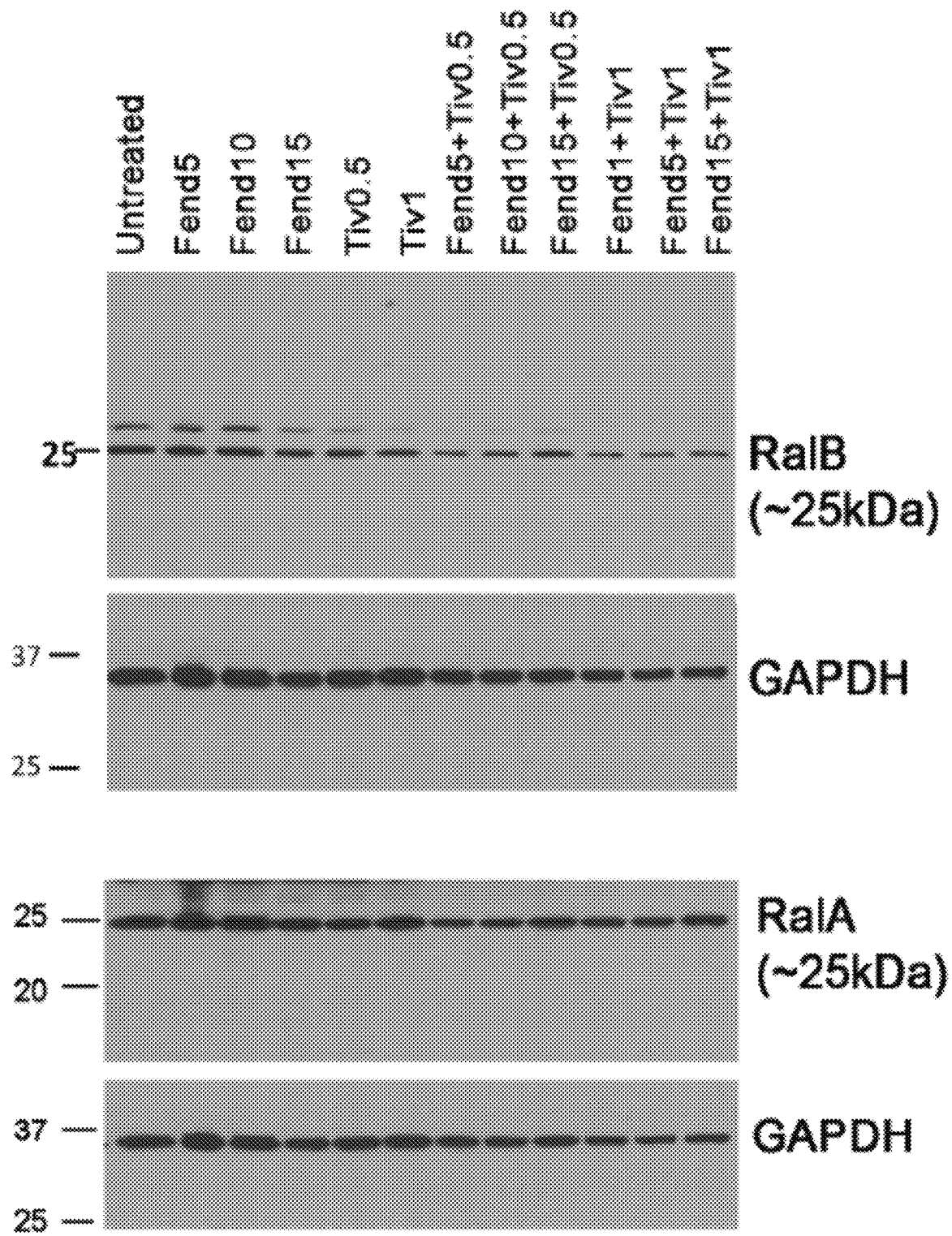

FIG. 12 shows images of representative blots that can demonstrate the effect of co-treatment of fendiline and tivantinib on the expression of RalB, which is a protein involved in membrane trafficking and can be important to tumor survival.

Figure 13:
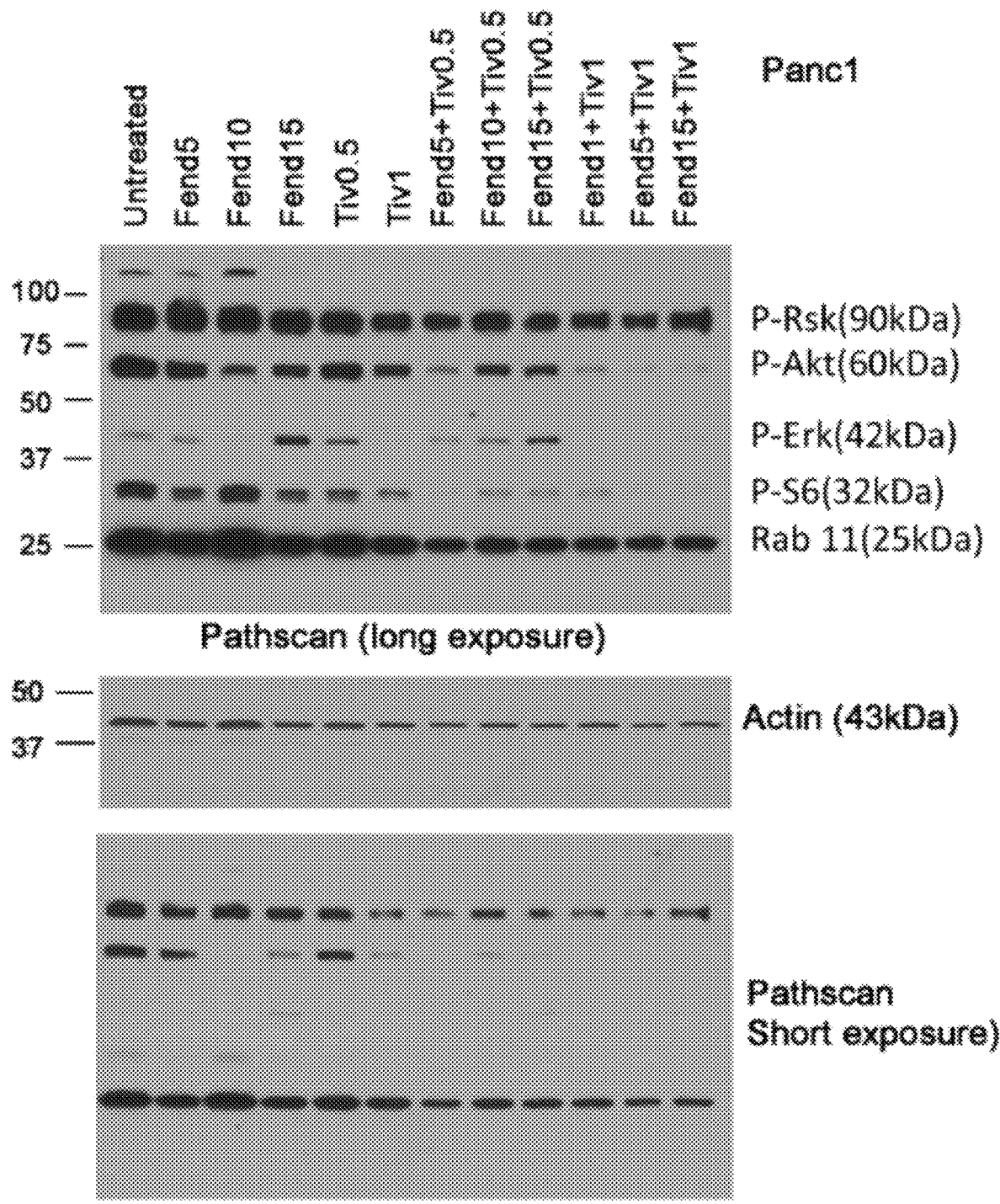

FIG. 13 shows images of representative blots that can demonstrate the effect of co-treatment with fendiline and tivantinib on kinases that are associated with survival and proliferative signaling cascade in Panc1 cells.

Figure 14:
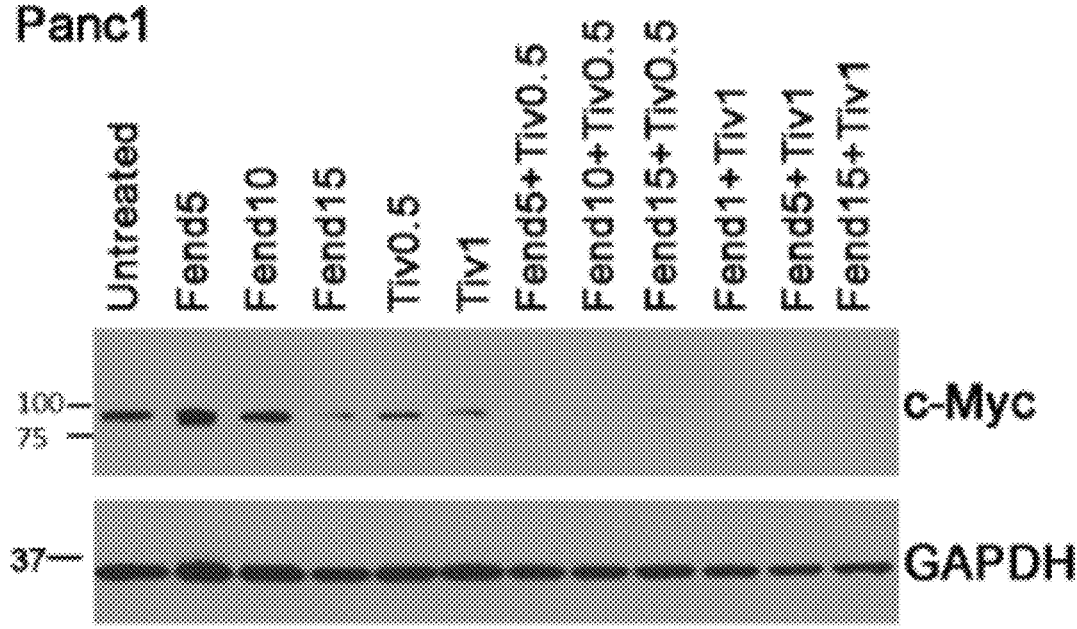

FIG. 14 shows an image of a representative blot that can demonstrate the effect of co-treatment with fendiline and tivantinib on c-Myc in Panc1 cells. C-Myc is a transcription factor that can play a role in cell cycle progression and cellular transformation.

Figure 15:
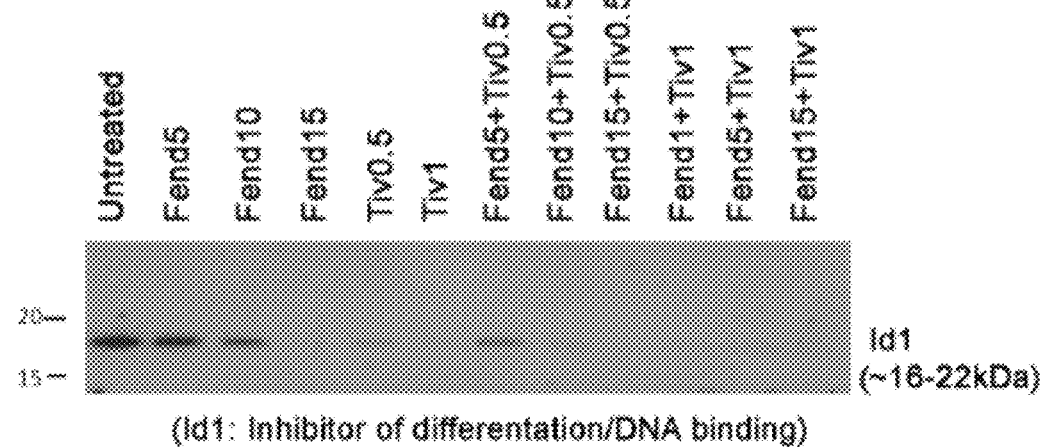

FIG. 15 shows an image of a representative blots that can demonstrate the effect of co-treatment with fendiline and tivantinib on Id1 and CD44 expression in Panc1 cells. Id1 is an inhibitor of differentiation and DNA binding. CD44 is a type I transmembrane glycoprotein that can mediate cell to cell and cell-matrix interactions.

Figures 16A, 16B:
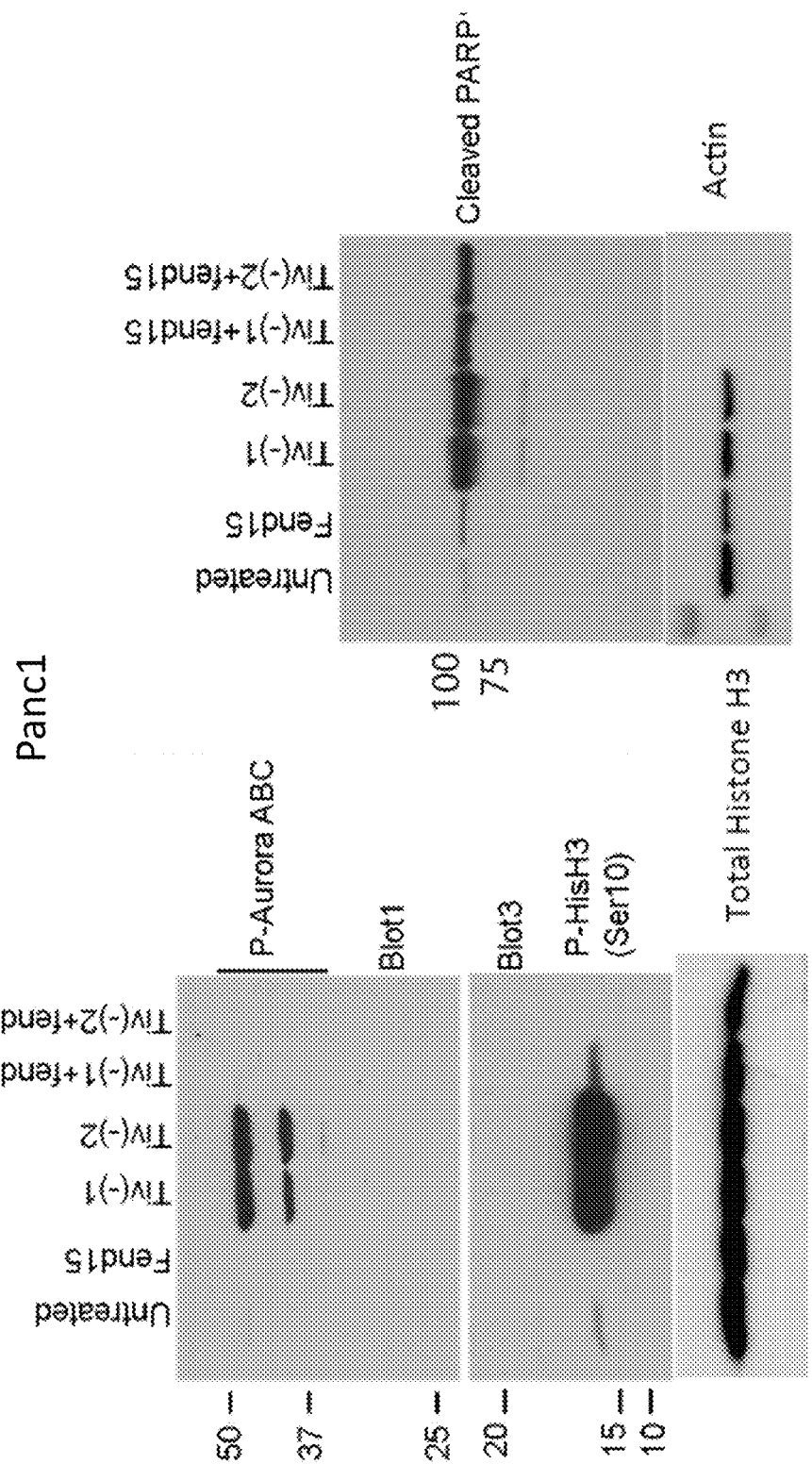

FIGS. 16A-16B show images of representative blots that can demonstrate the effect of co-treatment with fendiline and tivantinib on P-histone H3, P-Aurora ABC, and PARP cleavage in Panc1 cells.

Figure 17:
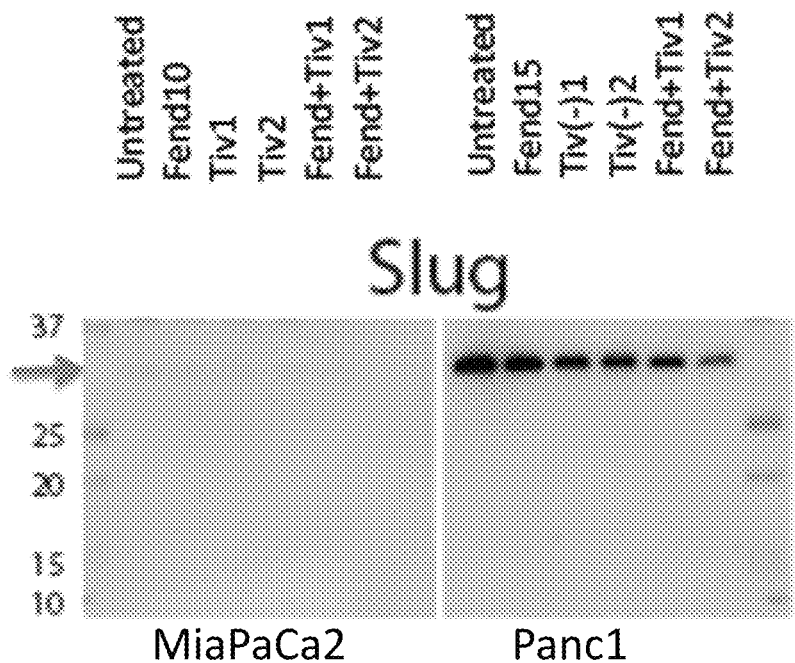

FIG. 17 shows images of representative blots that can demonstrate the effect of co-treatment with fendiline and tivantinib on Slug in MiaPaCa2 and Panc1 cells.

Figure 18:
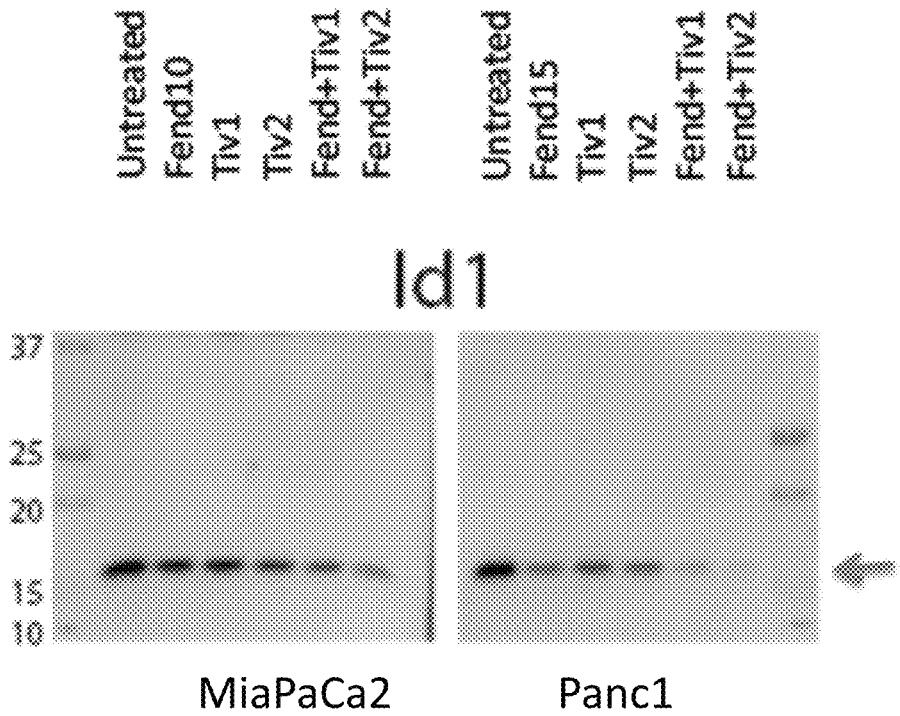

FIG. 18 shows images of representative blots that can demonstrate the effect of co-treatment with fendiline and tivantinib on Id1 in MiaPaCa2 and Panc1 cells.

Figure 19:
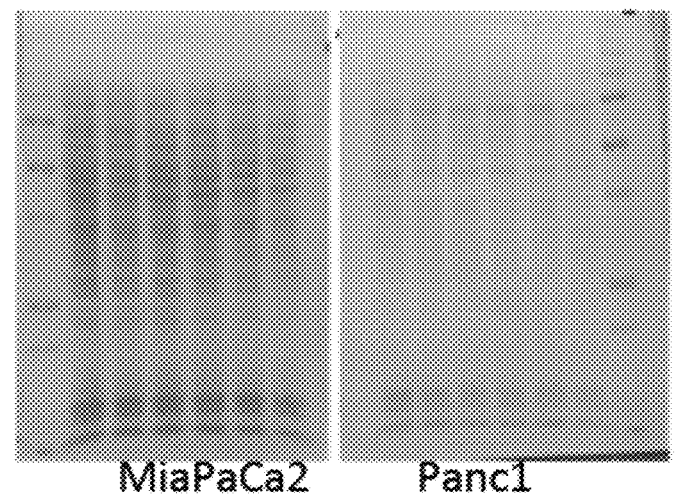

FIG. 19 shows an image of a gel stained with Ponceau S demonstrating protein load for the preparation of the blots that were probed and imaged and shown in FIGS. 17-18 and 20-24B, FIG. 20 shows images of representative blots that can demonstrate the effect of co-treatment with fendiline and tivantinib on Slug in Panc1 cells.

Figure 21:
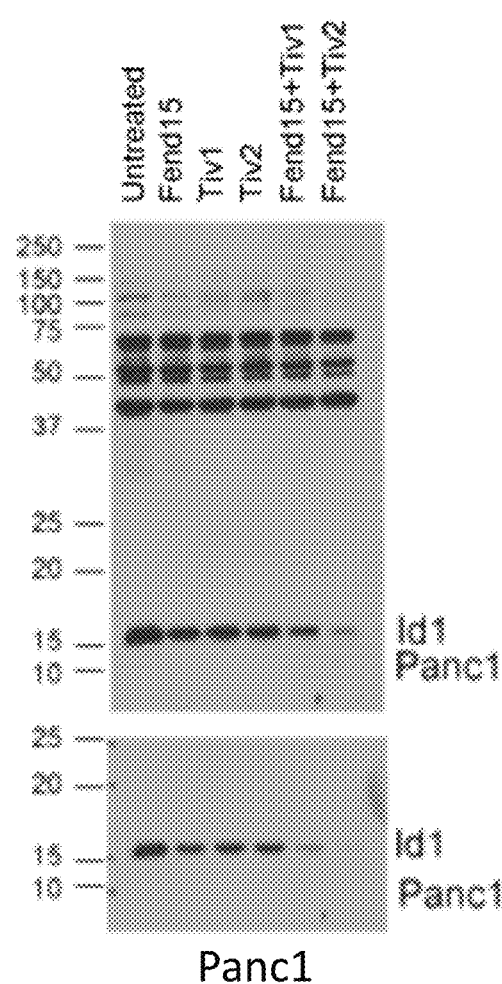

FIG. 21 shows images of representative blots that can demonstrate the effect of co-treatment with fendiline and tivantinib on Id1 in Panc1 cells.

Figures 22, 23:
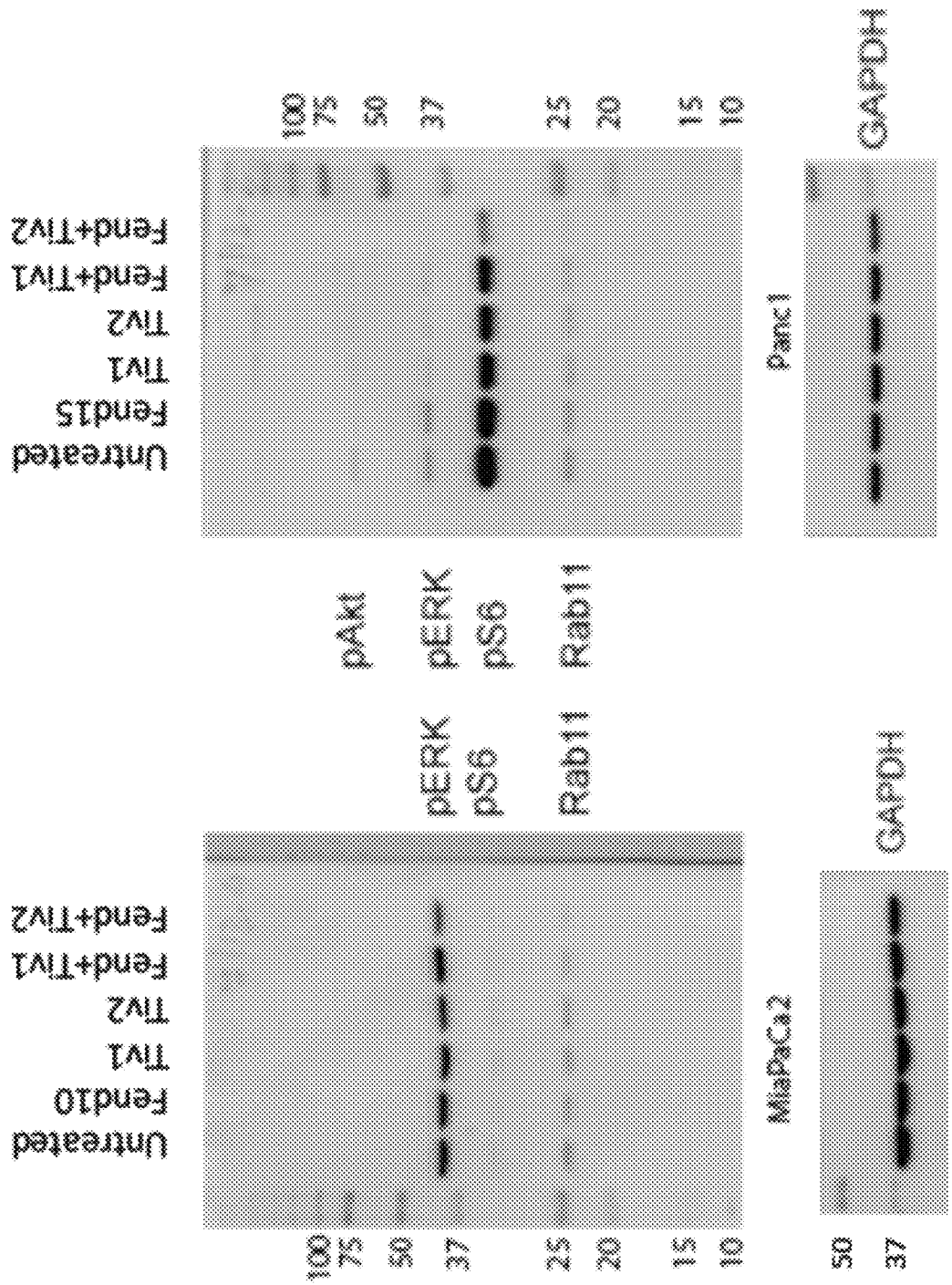

FIG. 22 shows images of representative blots that can demonstrate the effect of co-treatment with fendiline and tivantinib on pERK, pS6, and Rab11 in MiaPaCa2 cells.

FIG. 23 shows images of representative blots that can demonstrate the effect of co-treatment with fendiline and tivantinib on pERK, pS6, and Rab11 in Panc1 cells.

FIGS. 24A-24B show images of representative blots that can demonstrate the effect of co-treatment with fendiline and tivantinib on GSK3alpha/beta in MiaPaCa2 and Panc1 cells.

Figure 25:
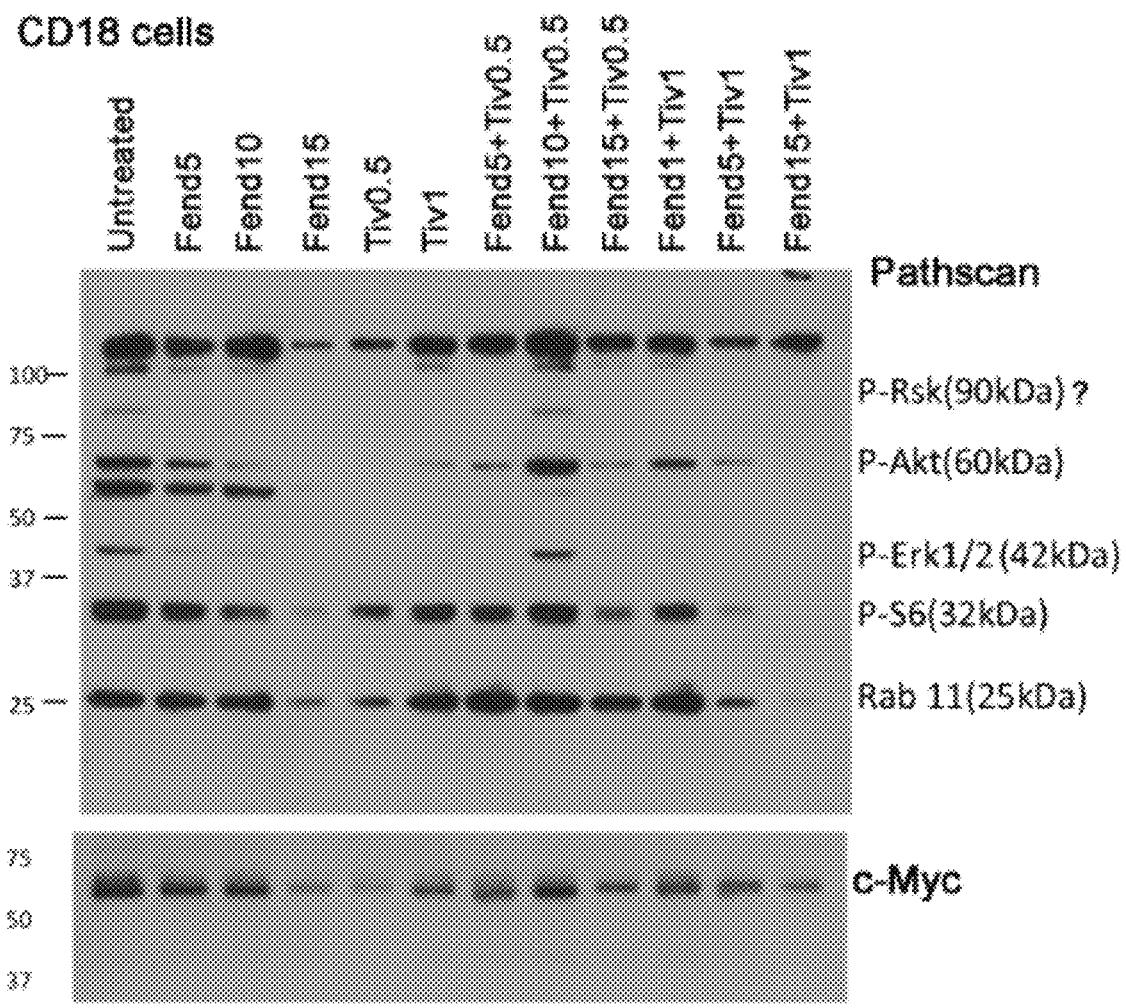

FIG. 25 shows an image of a representative blot that can demonstrate the effect of co-treatment with fendiline and tivantinib on p-Rsk, p-Akt, p-Erk1/2, p-S6, Rab, and c-Myc in CD18 cells.

FIGS. 26A-26C show fluorescent microscopic images of CD18 cells treated with fendiline or Tivantinib as compared to untreated after about 24 hours of treatment and staining with antibodies against p-Auorora ABC or a-tubulin and counterstained with Hoechst.

Figure 27:
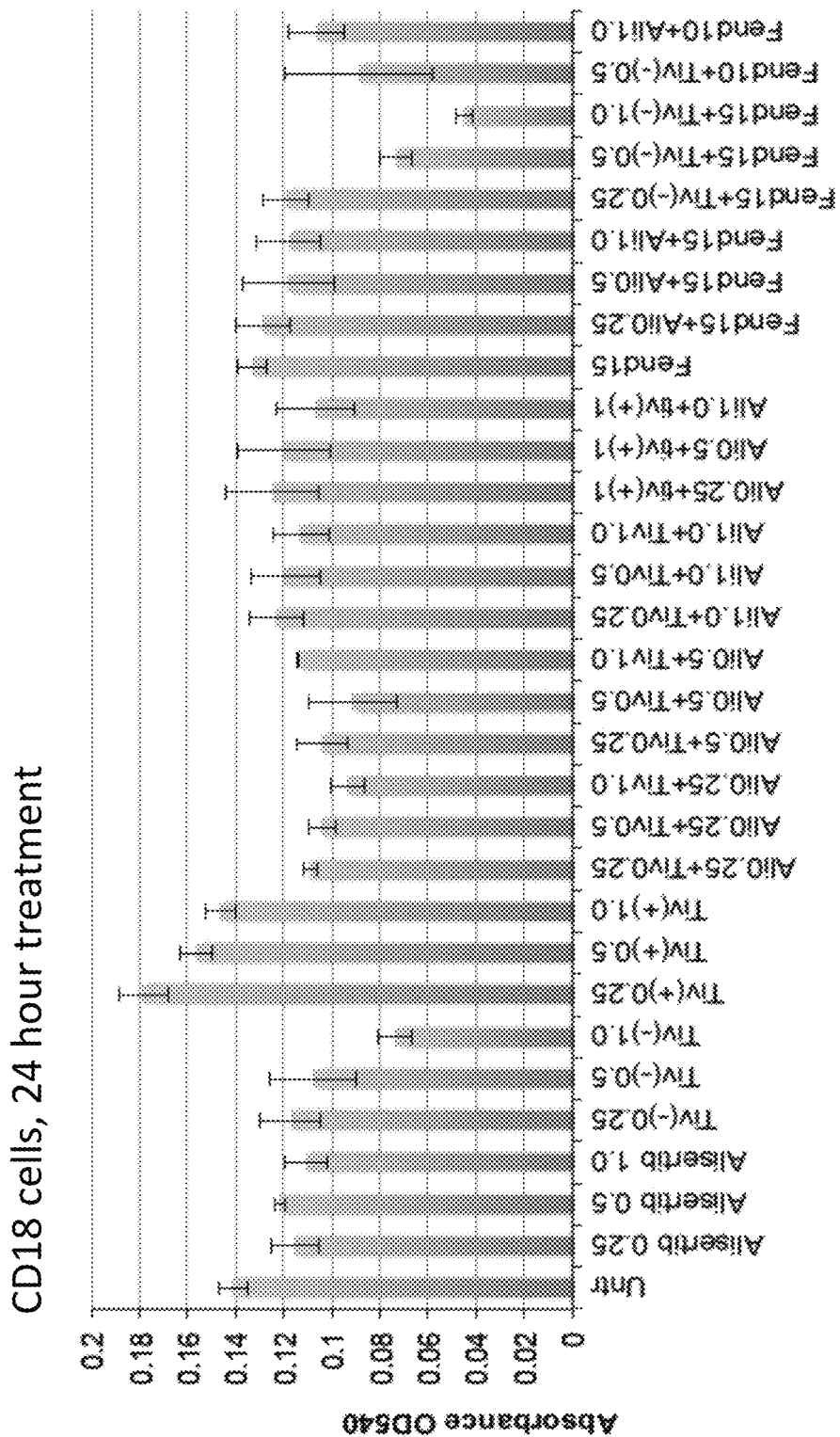

FIG. 27 shows a graph that can demonstrate the effect of co-treatment with an aurora-ABC inhibitor (alisertib) and tivantinib on CD18 cells.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, genetics, organic chemistry, biochemistry, biology, cell biology, cancer biology and the like, which are within the skill of the art. Such Definitions As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "administering" can refer to any administration route, including but not limited to, administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used herein "aurora ABC inhibitor," can refer to a compound that can inhibit the enzymatic activity of aurora kinase A, B, and/or C. Aurora ABC inhibitors can include, but are not limited to, ZM447439, VX-680, hesperidin, AMG 900, barasertib, ML141, AT9283, PF-03814735, Danusertib and alisertib.

As used herein, "autophagy inhibitor" refers to small molecule compounds that can be effective to reduce or eliminate macroautophagy (also referred to as autophagy) by inhibiting or eliminationg one or more steps in the autophagy process in a cell. Autophagy is a cellular process that is associated with the formation of an autophagosome that can fuse with a lysosome to become an autolysosome. The contents of the autophagosome are then degraded. The process plays a role in clearing damaged cell components and recycling autophagy-derived nutrients. Autophagy inhibitors include, but are not limited to, verteporfin, 3-methyladenine, bafilomyin A1, chloroquine, Wortmannin, LY294002, SB202190, SB203580, U0126, and SP600125.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "chemotherapeutic agent" or "chemotherapeutic" can refer to a therapeutic agent utilized to prevent or treat cancer and any other disease.

As used herein, the term "co-administering," "co-administered," "co-administer," and the like can refer to the administration, either in the same or different formulations and/or dosage forms, two or more different active ingredients (e.g. fendiline, a MET-inhibitor, an aurora ABC inhibitor, and an autophagy inhibitor) to a subject. The co-administration of the two or more different active ingredients can be administered simultaneously (i.e., at or about at the same time) or sequentially (e.g., at different times after one another, such as 1, 5, 10, 15, 20, 25, 30, 60 minutes, or 1, 2, 3, 4, 5, 6, 12, 18, 24, 36, 48, 72, 96 or more hours apart).

As used herein, "control" can refer to an alternative subject or sample used in an experiment for comparison purposes and included to minimize or distinguish the effect of variables other than an independent variable. A control can be positive or negative. One of ordinary skill in the art will appreciate what are appropriate controls for a given context.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "effective amount" can refer to an amount of a formulation provided herein sufficient to effect beneficial or desired results. An effective amount can be administered in one or more administrations, applications, or dosages. "Effective amount" can refer to a formulation provided herein that can treat or prevent pancreatic cancer or a symptom thereof. "Effective amount" can refer to a formulation provided herein that can treat or prevent a resistant pancreatic cancer or a symptom thereof. "Effective amount" can refer to the amount of a formulation provided herein that can kill a pancreatic cancer cell. "Effective amount" can refer to the amount of a formulation provided herein that can kill a resistant pancreatic cancer cell. The term "effective amount," as used herein, can also be used interchangeably with "pharmaceutically acceptable amount." Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician and effect as at least provided with respect to the term "effective amount". The effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "immunomodulator," can refer to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "least effective amount" can refer to the effective amount of a compound provided herein that is less than the amount the compound that would be administered and/or effective if that compound were to be administered alone and not as part of a combination therapy. "Least effective amount" can refer to the minimum effective amount of a compound, when administered alone or in combination with one or more additional active agents that can produce a desired effect (e.g. killing a pancreatic cancer cell (including, but not limited to, a resistant pancreatic cancer cell) and/or treating or preventing pancreatic cancer (including, but not limited to, a resistant pancreatic cancer). "Least effective amount" can refer to the minimum effective amount of a compound.

As used herein, "c-Met tyrosine kinase inhibitor" and its abbreviations "MET-inhibitor" and "c-MET inhibitors" can refer to small molecules that can inhibit the enzymatic activity of the c-Met tyrosine kinase. MET-inhibitors can include, but are not limited to, onartuzumab, foretinib, crizotinib, cabozantinib, and tivantinib.

As used herein, "mitigate" can refer to reducing a particular characteristic, symptom, or other biological or physiological parameter associated with a disease or disorder.

As used herein, "molecular weight" can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pancreatic cancer" can refer to cancer of the pancreas at any stage, including metastasized and non-metastasized pancreatic cancers.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring pancreatic cancer, pancreatic cancer metastases, or reducing a subject's risk of acquiring or reacquiring a pancreatic cancer or one or more of its attendant symptoms.

As used herein, "resistant pancreatic cancer," "resistant pancreatic cancer cell," and the like can refer to pancreatic cancer(s) and/or pancreatic cancer cells that are resistant and/or non-responsive to treatment with traditional chemotherapeutics and/or radiation therapy. "Resistant pancreatic cancer," "resistant pancreatic cancer cell," and the like can refer to pancreatic cancer(s) and/or pancreatic cancer cells that are resistant and/or non-responsive to treatment with gemcitabine and/or 5-fluorouracil (5-FU).

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects, such as treating or preventing pancreatic cancer, including resistant pancreatic cancer, or killing a pancreatic cancer cell, including a resistant pancreatic cancer.

As used herein, "synergistic effect," "synergism," or "synergy" can refer to an effect arising between two or more molecules, compounds, substances, factors, or compositions that that is greater than or different from the sum of their individual effects.

As used herein, "therapeutic", "treating", "treat," and the like can refer to include partially or completely delaying, alleviating, mitigating or reducing the intensity of one or more attendant symptoms of a pancreatic cancer including, but not limited to, a resistant pancreatic cancer. The terms, "therapeutic", "treating", "treat," and the like can also refer to killing one or more pancreatic cancer cells, including but not limited to, one or more resistant pancreatic cancer cells.

DISCUSSION

Pancreatic cancer is one of the deadliest types of cancer and is now the fourth leading causes of death in the United States. Pancreatic cancer is often diagnosed at a very late stage when the cancer is aggressive and metastasized, and is resistant to chemo and radiation-therapies. Compounding the effects of late diagnosis is that pancreatic cancers are or can become resistant to traditional chemotherapy and/or radiation therapies, particularly those where only a single chemotherapeutics are used. As such, there exists a need for improved therapies for pancreatic cancer.

With that said, described herein are combination formulations that can include an amount of fendiline and an amount of a MET inhibitor, an autophagy inhibitor, or an aurora ABC inhibitor. The combination formulations can be effective to kill a pancreatic cell and/or treat pancreatic cancer or symptom thereof in a subject in need thereof. Also provided herein are methods of killing a pancreatic cell and/or treating a pancreatic cancer or symptom thereof in a subject in need thereof that can include the step of co-administering an amount of fendiline and an amount of a MET inhibitor, an autophagy inhibitor, or an aurora ABC inhibitor. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this Description, and be within the Scope of the Present Disclosure.

Combinatorial Pharmaceutical Formulations

Provided herein are combinatorial formulations that can contain a combination of compounds that can be effective to kill a pancreatic cancer cell and/or a resistant pancreatic cancer cell. The formulations provided herein can contain an amount (e.g. an effective amount or least effective amount) of a calcium channel blocker and an amount of a MET-inhibitor, an autophagy inhibitor, or an aurora ABC inhibitor. The formulations provided herein can be used to treat or prevent pancreatic cancer. The formulations provided herein can contain an amount (e.g. an effective amount or least effective amount) of fendiline and an amount (e.g. an effective amount or least effective amount) of a MET-inhibitor, an autophagy inhibitor, or an aurora ABC inhibitor. In some embodiments, the formulations can contain an amount (e.g. an effective amount or least effective amount) of fendiline and an amount (e.g. an effective amount or least effective amount) of a MET-inhibitor. In some embodiments, the MET-inhibitor can be tivantinib. In some embodiments, the formulations can contain an amount (e.g. an effective amount or least effective amount) of fendiline and an amount (e.g. an effective amount or least effective amount) of an autophagy inhibitor. In some embodiments, the autophagy inhibitor can be verteporfin. In some embodiments, the formulations can contain an amount (e.g. an effective amount or least effective amount) of fendiline and an amount (e.g. an effective amount or least effective amount) of an aurora ABC inhibitor. In some embodiments, the aurora ABC inhibitor can be alisertib.

Pharmaceutically Acceptable Carriers and Auxiliary Ingredients and Agents

The combinatorial pharmaceutical formulations described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, si licic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In some embodiments, the only active agents contained in the formulation can be fendiline and a MET-inhibitor, an autophagy inhibitor, or an aurora ABC inhibitor. In other embodiments, in addition to the effective amount of a fendiline and a MET-inhibitor, an autophagy inhibitor, or an aurora ABC inhibitor described herein, the pharmaceutical formulation can also optionally include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, chemotherapeutics, antihypertensives, anticoagulants, and antiarrhythmics.

Effective Amounts of the Combination Formulations, Formulation Components, and Auxiliary Agents The effective amount or least effective amount of the combination formulation provided herein can range from 0.1 to 100 mg/kg of body weight. The effective amount or least effective amount of the combination formulation provided herein can range from 1 mg to about 10 g per dose. The effective amount or least effective amount of the combination formulation provided herein can range from 10 µL to about 10 mL per dose.

The effective amount or least effective amount of fendiline in the formulation can range from 0.1 to 100 mg/kg of body weight. The effective amount or least effective amount of the MET-inhibitor in the formulation can range from 0.1 to 100 mg/kg of body weight. The effective amount or least effective amount of the autophagy inhibitor can range from 0.1 to 100 mg/kg of body weight. The effective amount or least effective amount of the aurora ABC inhibitor can range from 0.1 to 100 mg/kg of body weight.

The effective amount or least effective amount of fendiline in the formulation can range from 1 mg to about 10 g per dose. The effective amount or least effective amount of the MET-inhibitor in the formulation can range from 1 mg to about 10 g per dose. The effective amount or least effective amount of the autophagy inhibitor can range from 1 mg to about 10 g per dose. The effective amount or least effective amount of the aurora ABC inhibitor can range from 1 mg to about 10 g per dose.

The effective amount or least effective amount of fendiline in the formulation can range from 10 µL to about 10 mL per dose. The effective amount or least effective amount of the MET-inhibitor in the formulation can range from 10 µL to about 10 mL per dose. The effective amount or least effective amount of the autophagy inhibitor can range from 10 µL to about 10 mL per dose. The effective amount or least effective amount of the aurora ABC inhibitor can range from 10 µL to about 10 mL.

One of skill in the art will appreciate that the exact volume will depend on, inter alia, the age and size of the subject, as well as the location of administration.

In embodiments where an optional auxiliary active agent is included in the pharmaceutical formulation, the therapeutically effective amount of the auxiliary active agent will vary depending on the auxiliary active agent. In some embodiments, the therapeutically effective amount of the optional auxiliary active agent can range from 0.001 micrograms to about 1000 milligrams. In other embodiments, the therapeutically effective amount of the optional auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the optional auxiliary active agent can range from about 1% w/w to about 50% w/w of the total pharmaceutical formulation. In additional embodiments, the therapeutically effective amount of the optional auxiliary active agent ranges from about 1% v/v to about 50% v/v of the total pharmaceutical formulation. In still other embodiments, the therapeutically effective amount of the optional auxiliary active agent ranges from about 1% w/v to about 50% w/v of the total pharmaceutical formulation.

Dosage Forms

In some embodiments, the pharmaceutical formulations described herein can be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations can be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 0.1 mg to 10 g or 1 µL to 10 mL or more of a pharmaceutical formulation containing an effective amount or an appropriate fraction thereof of each of the fendiline and MET-inhibitor, autophagy inhibitor, or the aurora ABC inhibitor. The oral dosage form can be administered to a subject in need thereof by a suitable administration method.

Where appropriate, the dosage forms described herein can be microencapsulated. The dosage form can also be prepared to prolong or sustain the release of any ingredient. In some embodiments, the fendiline, MET-inhibitor, autophagy inhibitor, and/or the aurora ABC inhibitor can be the ingredient(s) whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the fendiline and MET-inhibitor, autophagy inhibitor, the aurora ABC inhibitor, and/or optional auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the fendiline and MET-inhibitor, autophagy inhibitor, the aurora ABC inhibitor, and/or the optional auxiliary active ingredient, in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the fendiline and MET-inhibitor, autophagy inhibitor, the aurora ABC inhibitor, and/or the auxiliary active agent, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of the combination formulation containing fendiline and MET-inhibitor, autophagy inhibitor, the aurora ABC inhibitor, and/or the optional auxiliary active agent. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses or more are delivered each time.

For some dosage forms suitable and/or adapted for inhaled administration, the pharmaceutical formulation is a dry powder inhalable formulation. In addition to the fendiline and MET-inhibitor, autophagy inhibitor, or the aurora ABC inhibitor, and an optional auxiliary active ingredient, and/or pharmaceutically acceptable salt thereof, such a dosage form can contain a powder base such as lactose, glucose, trehalose, manitol, and/or starch. In some of these embodiments, fendiline and MET-inhibitor, autophagy inhibitor, the aurora ABC inhibitor, optional auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the fendiline, the MET-inhibitor, the autophagy inhibitor, or the aurora ABC inhibitor described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraocular, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents. For some embodiments, the dosage form contains a predetermined amount of the combination formulations provided herein per unit dose. In an embodiment, the predetermined amount of the combination formulations provided herein can be an effective amount or least effective amount of the combination formulation provided herein or component thereof. In other embodiments, the predetermined amount of the combination formulation provided herein can be an appropriate fraction of the effective amount of each of active ingredients. Such unit doses may therefore be administered once or more than once a day. Such pharmaceutical formulations may be prepared by any of the methods well known in the art.

Methods of Treating Pancreatic Cancer

The combination formulations provided herein can be used to kill a pancreatic cancer cell including, but not limited to, a resistant pancreatic cell. The combination formulations provided herein can be used to treat or prevent pancreatic cancer or symptom thereof in a subject in need thereof. The subject in need thereof can have pancreatic cancer. In some embodiments, the pancreatic cancer is a resistant cancer. In some embodiments, the combination formulations can result in an additive or synergistic effect between the one or more components provided in the formulation. In some embodiments, the combination of components in the combination formulations provided herein can result in a lower dose of each individual components being administered and/or can also result in an increased cytotoxicity as compared to any one individual components alone.

Provided herein are methods of treating and/or preventing pancreatic cancer in a subject in need there of or killing a pancreatic cancer cell in a subject in need thereof that can contain the step of co-administering an amount (e.g. an effective or least effective amount) of fendiline and an amount (e.g. an effective or least effective amount) of a MET-inhibitor, an autophagy inhibitor, or an aurora ABC inhibitor, to the subject in need thereof. In some embodiments the method can include administering an amount of a formulation provided herein that can contain amount (e.g. an effective or least effective amount) of fendiline and an amount (e.g. an effective or least effective amount) of a MET-inhibitor, an autophagy inhibitor, or an aurora ABC inhibitor.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Figure 1:
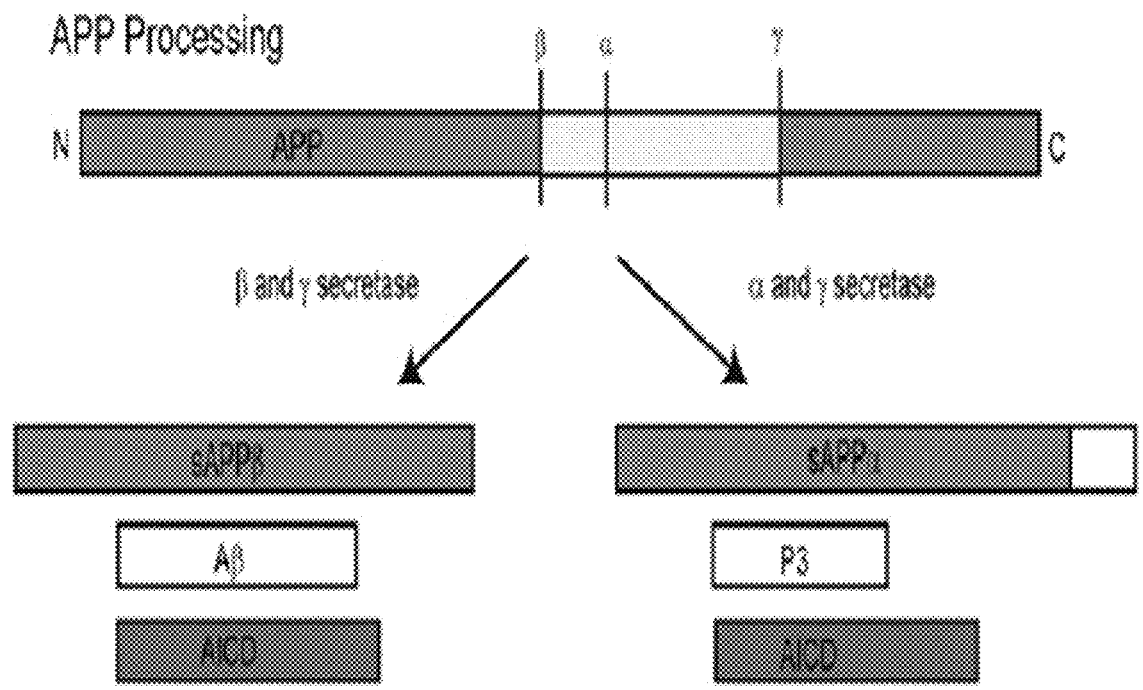
FIG. 1 shows a schematic representation of APP processing in pancreatic cancer cells by ADAM10 ($\alpha$-secretase) $\beta$-secretase (BACE), and $\gamma$-secretase. ADAM10 cleavage, followed by g-secretase cleavage produces sAPP$\alpha$, P3 and amyloid precursor protein intracellular domain (AICD). BACE followed by $\gamma$-secretase cleavage leads to the amyloidogenic pathway involving the conversion of APP to sAPP$\beta$, and A$\beta$ and AICD.

ADAM10 is a known α-secretase that cleaves APP in the non-amyloidogenic pathway to generate the growth promoting fragment of APP, sAPPα. It has been shown that pancreatic cancer cells express high levels of ADAM10 and cleave APP generating increased levels of sAPPα. It has been shown that combinatorial treatment with ADAM10 inhibitor Batimastat and nucleoside analogue Gemcitabine resulted in enhanced cytotoxicity and cell death in cancer cells. It is known that ADAM10 is activated in response to $Ca^{2+}$ activation and we showed recently that the calcium channel blocker fendiline inhibits ADAM10, and induces cytotoxicity in cancer cells. FIG. 1 shows a schematic representation of APP processing in pancreatic cancer cells by ADAM10 (α-secretase) β-secretase (BACE), and γ-secretase. ADAM10 cleavage, followed by g-secretase cleavage produces sAPPα, P3 and amyloid precursor protein intracellular domain (AICD). BACE followed by γ-secretase cleavage leads to the amyloidogenic pathway involving the conversion of APP to sAPPβ, and AR and AICD. This Example shows effects of combination treatments that can include fendiline in pancreatic cancer cells.

Methods

Pancreatic cancer cell line MiaPaCa2 and Panc1 were grown in DMEM with 10% fetal bovine serum and 1% penicillin-streptomycin.

Western Blotting and Antibodies:

Cell lysates were prepared with 200 μl of 1× Sample Buffer. Equal amounts of protein from each sample was loaded onto a 12% SDS-PAGE gel and then transferred onto a nitrocellulose membrane. The membranes were blocked with 5% milk in TBS for 1 hour and then probed with various primary antibodies overnight. The blots were washed with 1×PBST (PBS, 0.05% Tween-20) four times 5 minutes each and then incubated in secondary antibody for 1 hour 30 minutes. Successively, the blots were washed four times 5 minutes each in 1×PBST. The protein detection was done with SuperSignal West Pico Luminol reagent. Different primary antibodies used were 1:1000 dilutions of ADAM10, CD44, c-myc, cyclinD1, APP, sAPPα, cAPP and 1:10000 dilutions of Actin.

MTT Cell Toxicity Assay:

About 3000 cells were plated in each well of a 96 well plate, 1 blank and 1 control in quadruplicates. One plate was incubated for 24 hours and the other for 48 hours. At the end of the treatment, 100 μl of 1 mg/ml Thiazoyl Blue Tetrazolium Bromide (MTT) was pipetted into each of the wells except the blank and then incubated for 2 hours at 37° C. Subsequently, solution from the wells were removed and the purple formazan crystals formed were solubilized using 125 ml of isopropanol containing 4 mM HCl and 0.1% Nonidet P-40. The plate was placed on a shaker for 20 minutes and then the absorbance for each of the wells were measured at 540 nm.

Cell Migration Assay:

Cells were plated in a 12 well plate and incubated until the plates became fully confluent. A scratch was made along the diameter of each plate and new media containing different treatments were added. Pictures were taken soon after the wounds were made and after a 24 hour incubation period.

Results

Figure 2:
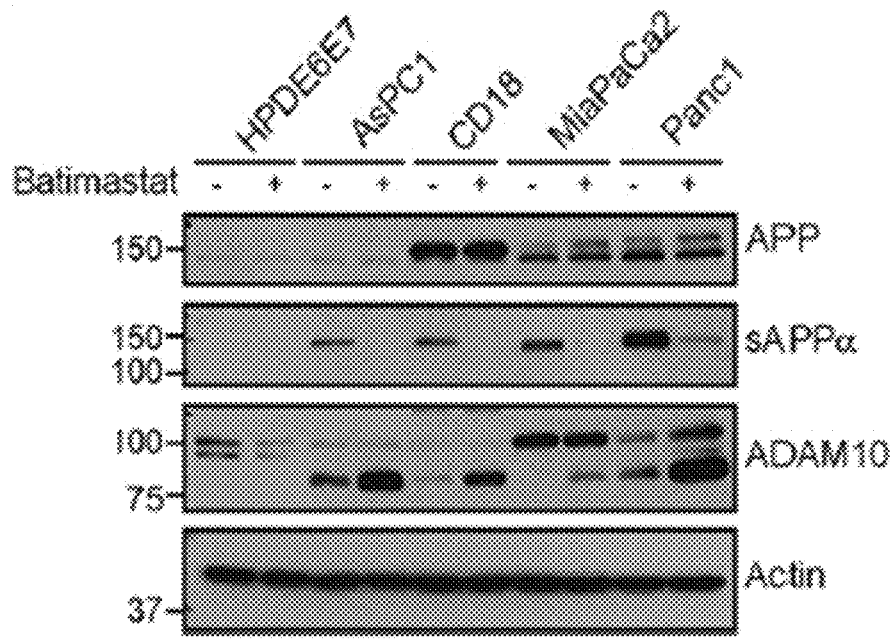
FIG. 2 shows an image of a representative blot that can demonstrate expression and secretion of sAPP$\alpha$ and expression of ADAM10 in the presence or absence of batimasta in cancer cell lines AsPC1, CD18, MiaPaCa2, and Panc1 and normal pancreatic cells, HPDE6E7.

FIG. 2 shows an image of a representative blot that can demonstrate expression and secretion of sAPPα and expression of ADAM10 in the presence or absence of batimasta in cancer cell lines AsPC1, CD18, MiaPaCa2, and Panc1 and normal pancreatic cells, HPDE6E7.

Figure 3:
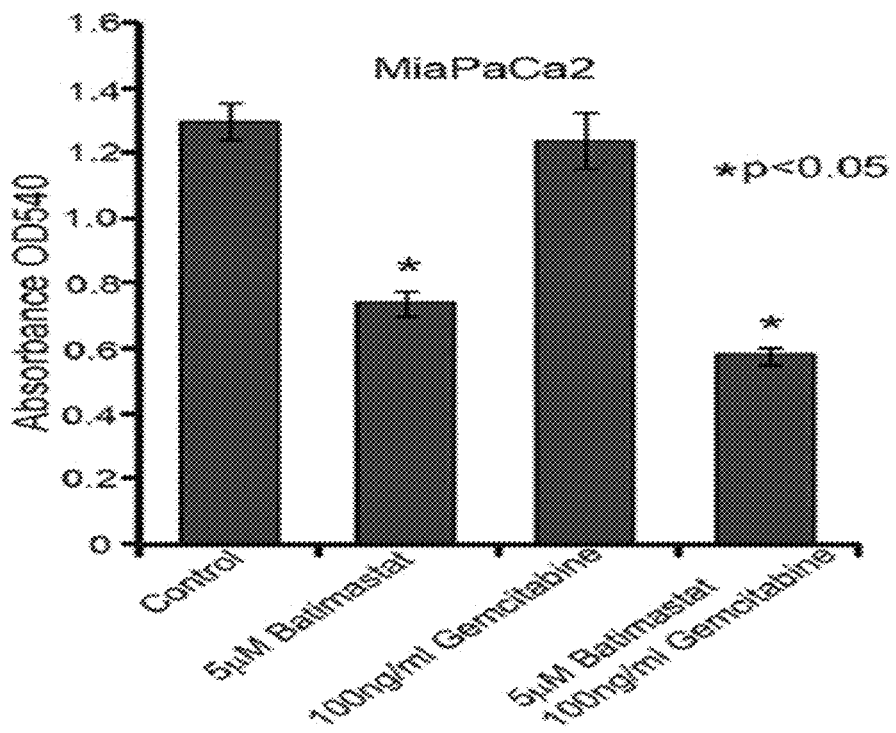
FIG. 3 shows a graph that can demonstrate that ADAM10 inhibition sensitizes MiaPaCa2 cells to gemcitabine. Cell survival among cells treated with Batimastat, Gemcitabine or a combination of Batimastat and Gemcitabine showed a decrease in cell survival in cells co-treated or singly treated with batimastat.

FIG. 3 shows a graph that can demonstrate that ADAM10 inhibition sensitizes MiaPaCa2 cells to gemcitabine. Cell survival among cells treated with Batimastat, Gemcitabine or a combination of Batimastat and Gemcitabine showed a decrease in cell survival in cells co-treated or singly treated with batimastat.

Figure 4A:
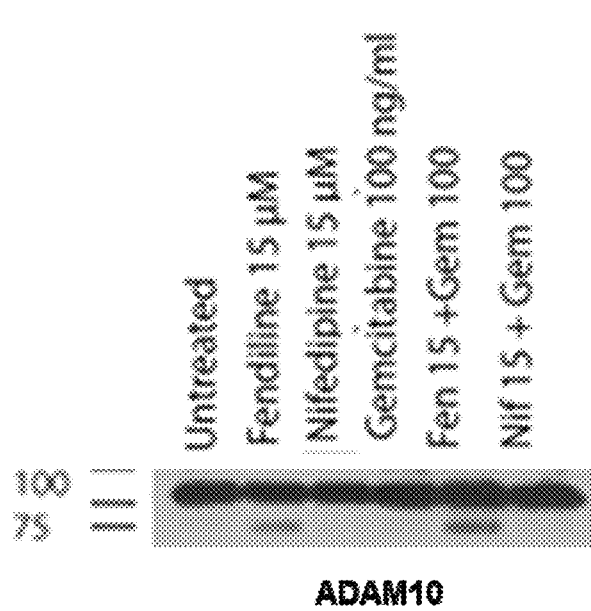
FIGS. 4A-4B shows images of representative blots that can demonstrate that calcium channel inhibitors increase the intermediate cleavage of ADAM10 (FIG. 4A) to generate the inactive about 80 kDa fragment.
Figure 4B:
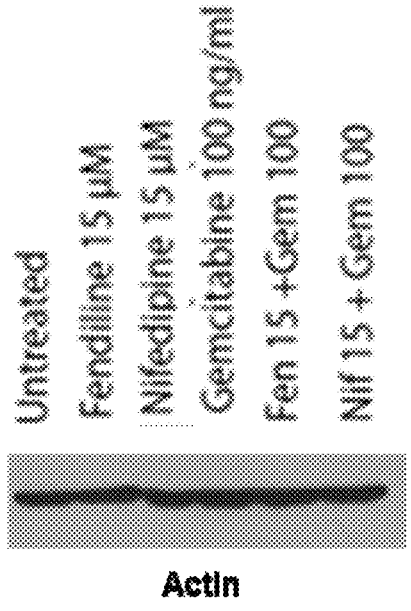
Figure 6A:
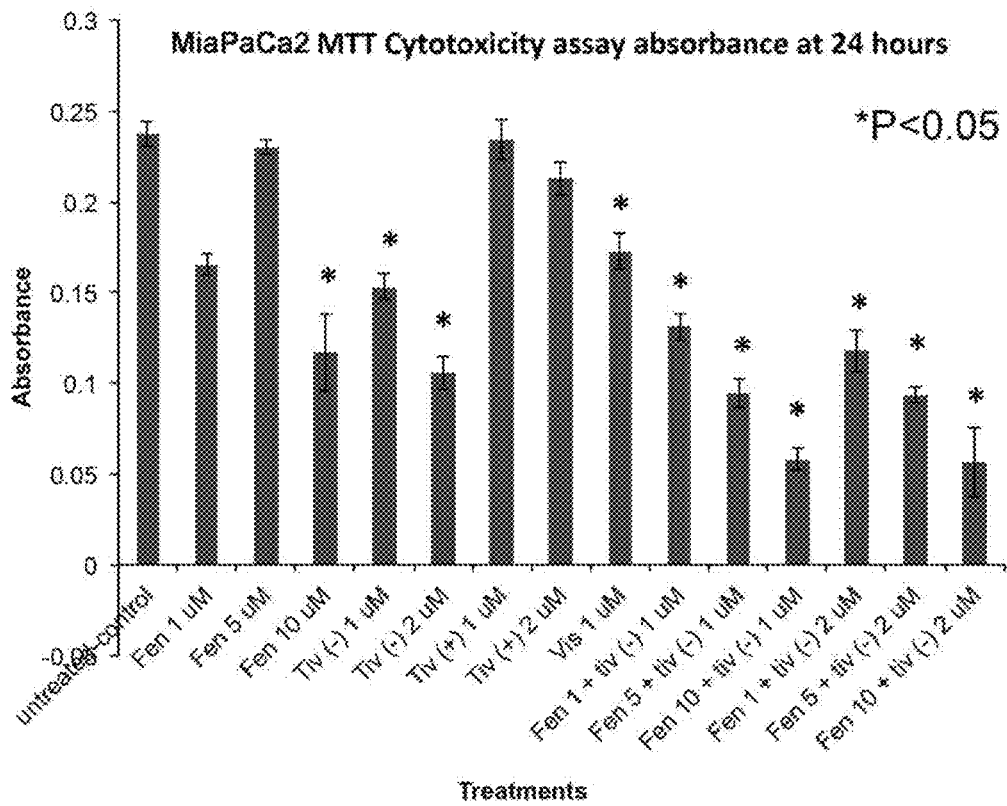
FIGS. 6A-6D show graphs that can demonstrate enhanced cytotoxicity in MiaPaCa2 and Panc1 cells treated with fendiline and tivantinib. MiaPaCa2 (FIGS. 6A-6B) and Panc1 (FIGS. 6C-6D) cells were treated with fendiline (1-15 mM) or tivantinib (1 or 2 mM) alone or in combination for 24 or 48 hours and cytotoxicity was analyzed using MTT assay.
Figure 6B:
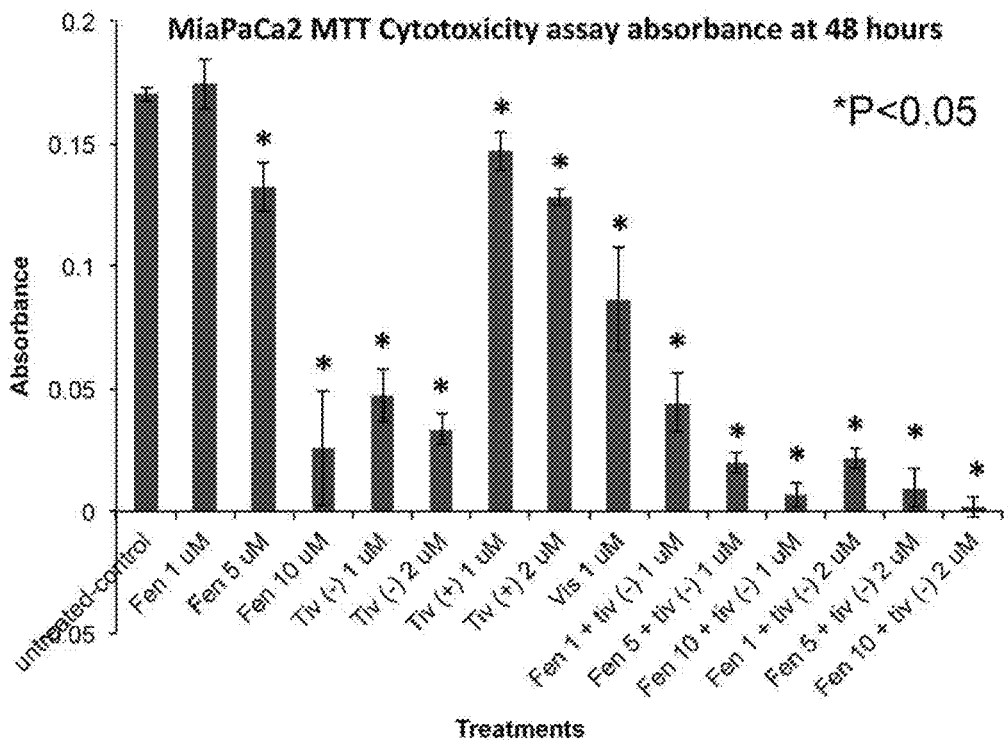
Figure 6C:
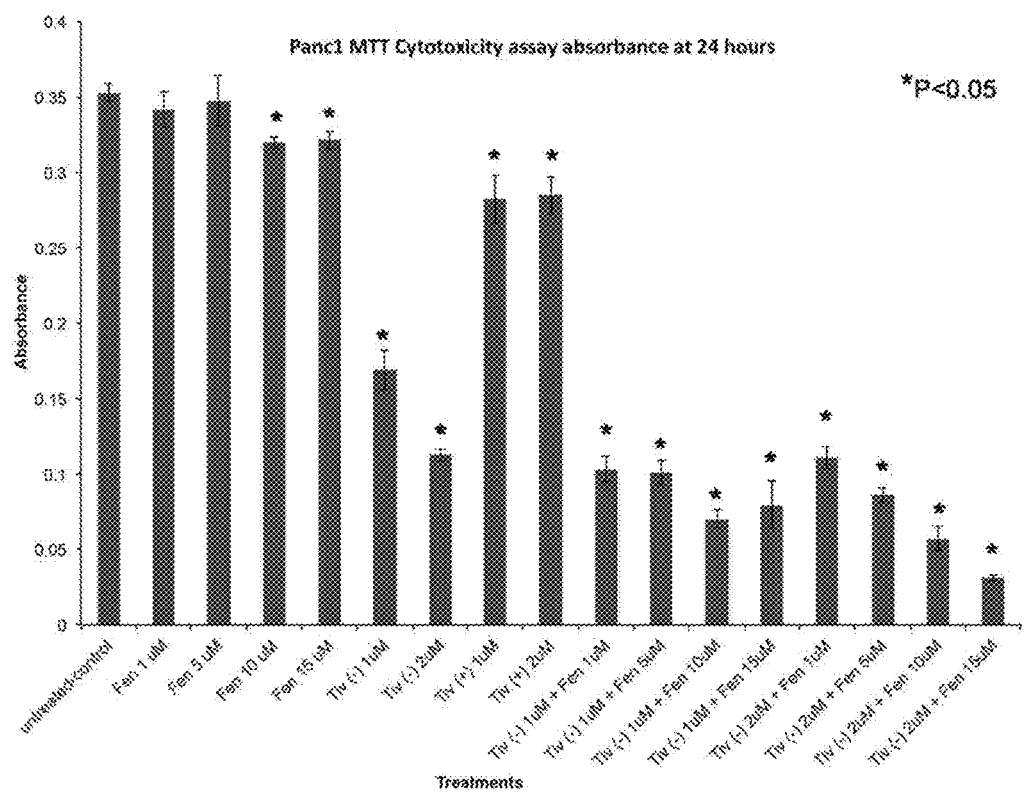
Figure 6D:
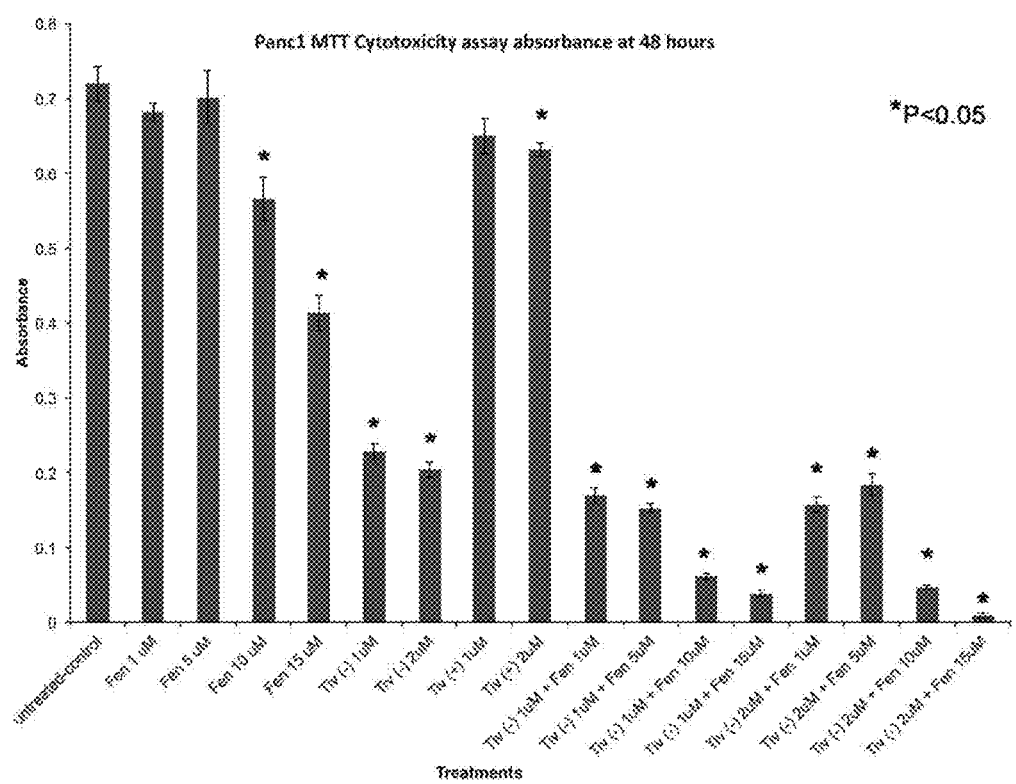

FIGS. 4A-4B shows images of representative blots that can demonstrate that calcium channel inhibitors increase the intermediate cleavage of ADAM10 (FIG. 4A) to generate the inactive about 80 kDa fragment. FIG. 4B shows an image of a blot that was reprobed with actin antibody for protein normalization.

FIGS. 5A-5E show images of representative blots that can demonstrate that Tivantinib and Fendiline decreases the expression of (FIG. 5A) CD44, (FIG. 5B) c-myc, and (FIG. 5D) cyclin D1 which are important for cancer cell migration and proliferation. FIGS. 5C and 5E show blots that were reprobed with actin antibody for protein normalization.

FIGS. 6A-6D show graphs that can demonstrate enhanced cytotoxicity in MiaPaCa2 and Panc1 cells treated with fendiline and tivantinib. MiaPaCa2 (FIGS. 6A-6B) and Panc1 (FIGS. 6C-6D) cells were treated with fendiline (1-15 mM) or tivantinib (1 or 2 mM) alone or in combination for 24 or 48 hours and cytotoxicity was analyzed using MTT assay.

FIGS. 7A-7H show microscopic images that can demonstrate cell morphology cell morphology differences, which can be indicative of apoptosis, upon treatment with varying concentrations of fendiline and tivantinib in Panc1 cells.

FIGS. 8A-8L show images of MiaPaCa2 cell treated with various calcium channel blockers. MiaPaCa2 cells were plated to confluency, growth arrested by serum starvation, and scratch wound was made. Cell culture medium with or without different calcium channel blockers at the indicated concentrations was added to the cells and images were taken immediately after the wound was made or after 24 hours.

Figure 9:
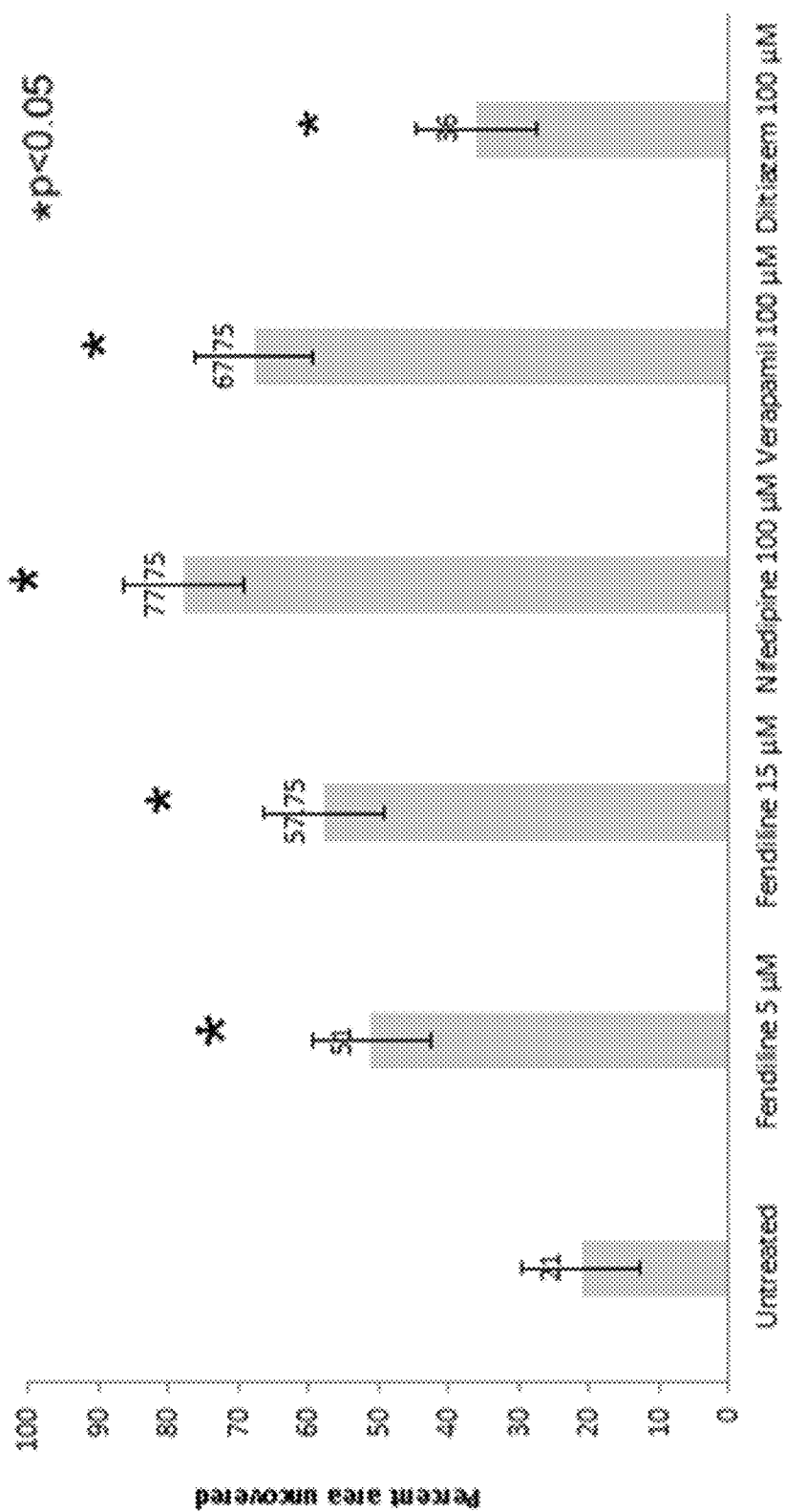
FIG. 9 shows a graph that can demonstrate percent area uncovered of the scratch wound from the images taken immediately after the treatments and at about 24 hours, which can provide an insight into the role of aberrant calcium signaling in migration of cancer cells.
Figure 10:
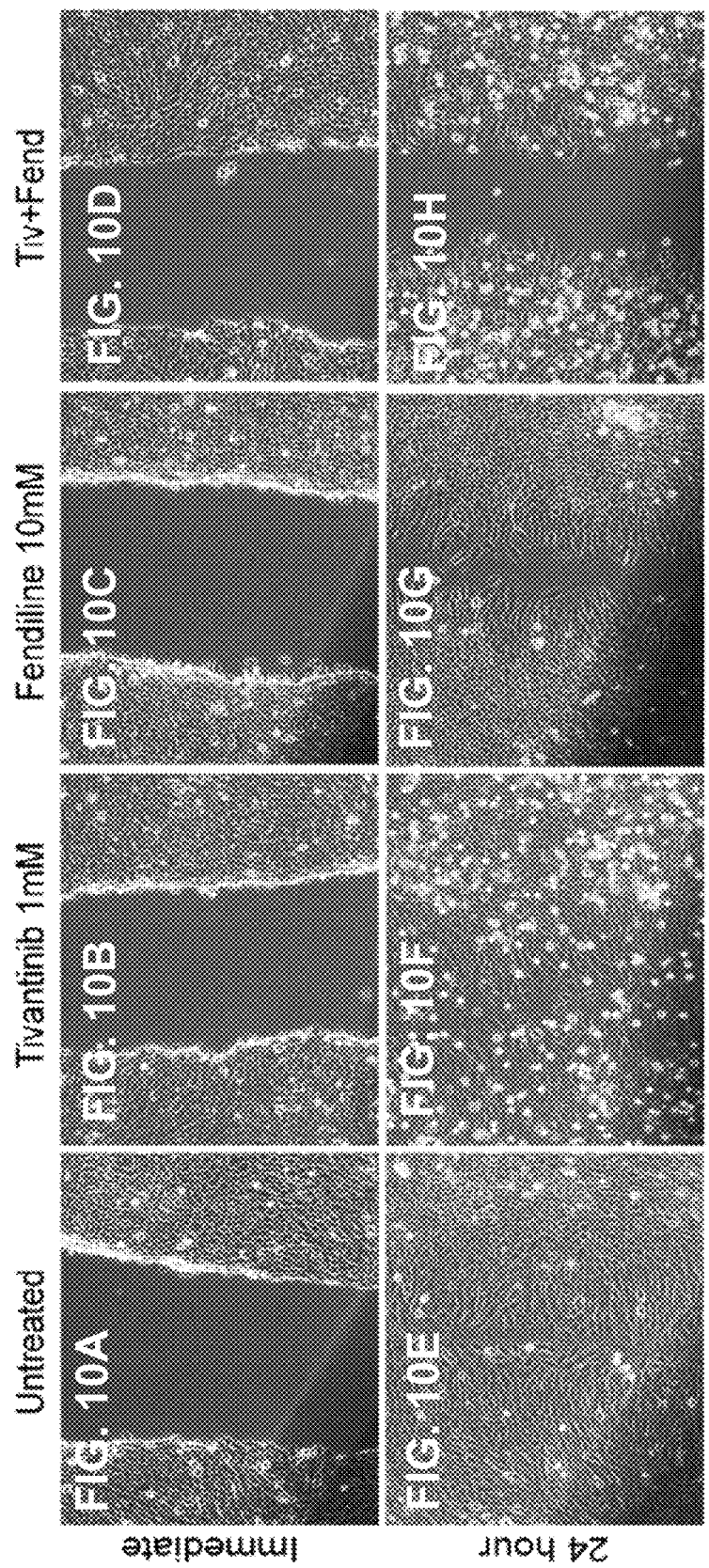
FIGS. 10A-10H show microscopic images that can demonstrate an effect of fendiline and tivantinib on Panc1 cells.

FIG. 9 shows a graph that can demonstrate percent area uncovered of the scratch wound from the images taken immediately after the treatments and at about 24 hours, which can provide an insight into the role of aberrant calcium signaling in migration of cancer cells.

FIGS. 10A-10H show microscopic images that can demonstrate an effect of fendiline and tivantinib on Panc1 cells. Panc1 cells were plated to confluency, growth arrested by serum starvation, and scratch wound was made. Cell culture medium with or without fendiline and tivantinib at the indicated concentration was added to the cells and images were taken immediately after the wound was made or after 24 hours.

Example 2

In this example, pancreatic cancer cells (CD18 (also known as HPAF18) cells, MiaPaCa2 cells, and Panc1 cells, were treated with various co-treatments that include fendiline and various biological effects were evaluated. In addition to in vitro evaluation of the combination treatments, the effect of the combination treatments on in vivo tumor growth using Pancreatic Ductal AdenoCarcinoma (PDAC) subcutaneous xenograft models were used in some cases.

Results

The effect of co-treatment with fendiline and tivantinib on Slug and RalB expression in PDAC cells (Panc1) was evaluated FIG. 11 shows images of representative blots that can demonstrate the effect of co-treatment of fendiline and tivantinib on the expression of Slug, which is a transcriptional repressor that can bind to the integrin promoter and decrease cell adhesion. FIG. 12 shows images of representative blots that can demonstrate the effect of co-treatment of fendiline and tivantinib on the expression of RalB, which is a protein involved in membrane trafficking and can be important to tumor survival. It was observed that co-treatment with fendiline and tivantinib can show an additive inhibition of Slug and RalB.

The effect of co-treatment with fendiline and tivantinib on the expression of various kinases associated with survival and a proliferative signaling cascade was examined using a Pathscan antibody cocktail from Cell signaling and a long exposure time. pRsk and pAkt are involved in cell proliferation, Rab11 is involved in vesicular trafficking and pS6 is an indicator of translation. FIG. 13 shows images of representative blots that can demonstrate the effect of co-treatment with fendiline and tivantinib on kinases that are associated with survival and proliferative signaling cascade in Panc1 cells.

The effect of co-treatment with fendiline and tivantinib on the expression of c-Myc was observed. c-Myc is a transcription factor that can play a role in cell cycle progression and cellular transformation. FIG. 14 shows an image of a representative blot that can demonstrate the effect of co-treatment with fendiline and tivantinib on c-Myc in Panc1 cells. C-Myc is a transcription factor that can play a role in cell cycle progression and cellular transformation. It was observed that there can be an additive inhibition of c-Myc by the co-treatment.

The effect of co-treatment with fendiline and tivantinib on the expression of Id1 and CD44 expression in Panc1 cells. FIG. 15 shows an image of a representative blots that can demonstrate the effect of co-treatment with fendiline and tivantinib on Id1 and CD44 expression in Panc1 cells. Id1 is an inhibitor of differentiation and DNA binding. CD44 is a type I transmembrane glycoprotein that can mediate cell to cell and cell-matrix interactions. It was observed that there can be an additive inhibition of Id1 and CD44 by the co-treatment.

The effect of co-treatment with fendiline and tivantinib on the expression of P-aurora ABC, p-His3, ancleavage of PARP. FIGS. 16A-16B show images of representative blots that can demonstrate the effect of co-treatment with fendiline and tivantinib on P-histone H3, P-Aurora ABC, and PARP cleavage in Panc1 cells. These results can indicate that co-treatment can interfere with histone and aurora ABC phosphorylation.

FIG. 17 shows images of representative blots that can demonstrate the effect of co-treatment with fendiline and tivantinib on Slug in MiaPaCa2 (Mia) and Panc1 cells.

FIG. 18 shows images of representative blots that can demonstrate the effect of co-treatment with fendiline and tivantinib on Id1 in MiaPaCa2 (Mia) and Panc1 cells.

Figure 20:
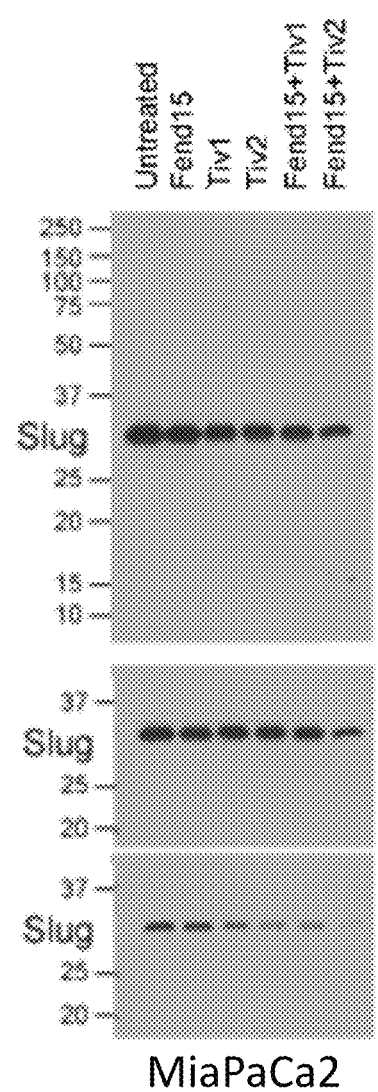

FIG. 20 shows images of representative blots that can demonstrate the effect of co-treatment with fendiline and tivantinib on Slug in Panc1 cells.

FIG. 21 shows images of representative blots that can demonstrate the effect of co-treatment with fendiline and tivantinib on Id1 in Panc1 cells. These results can demonstrate that co-treatment can inhibit both Id1 and Slug in pancreatic cancer cells.

FIG. 22 shows images of representative blots that can demonstrate the effect of co-treatment with fendiline and tivantinib on pERK, pS6, and Rab11 in MiaPaCa2 cells.

FIG. 23 shows images of representative blots that can demonstrate the effect of co-treatment with fendiline and tivantinib on pERK, pS6, and Rab11 in Panc1 cells. These results can demonstrate that co-treatment can inhibit pERK, pS6, and Rab11, which can indicate interference in proliferation, protein synthesis, and vesicular trafficking in treated cells.

FIGS. 24A-24B show images of representative blots that can demonstrate the effect of co-treatment with fendiline and tivantinib on GSK3alpha/beta in MiaPaCa2 and Panc1 cells. Phosphorylation of GSK3alpha at Ser21 and beta at Ser9 are associated with inhibition of the kinases, the antibody detects Ser21 and Ser9 phosphorylation on GSK3 alpha (51 kDa_ and beta (46 kDa), respectively. These results can demonstrate that co-treatment can inhibit GSK3alpha/beta in pancreatic cancer cells.

FIG. 19 shows an image of a gel stained with Ponceau S demonstrating protein load for the preparation of the blots that were probed and imaged and shown in FIGS. 17-18 and 20-24B.

FIG. 25 shows an image of a representative blot that can demonstrate the effect of co-treatment with fendiline and tivantinib on p-Rsk, p-Akt, p-Erk1/2, p-S6, Rab, and c-Myc in CD18 cells. These results can demonstrate that co-treatment can inhibit survival and proliferative signaling in pancreatic cancer cells.

FIGS. 26A-26C show fluorescent microscopic images of CD18 cells treated with fendiline or Tivantinib as compared to untreated after about 24 hours of treatment and staining with antibodies against p-Aurora ABC or a-tubulin and counterstained with Hoechst. These results can demonstrate that fendiline can inhibit aurora ABC phosphorylation.

FIG. 27 shows a graph that can demonstrate the effect of co-treatment with an aurora-ABC inhibitor (alisertib) and tivantinib on CD18 cells.

I claim:

1. A method of treating a pancreatic cancer that is resistant to or non-responsive to treatment with gemcitabine, 5-fluorouracil (5-FU), or gemcitabine and 5-FU or a symptom thereof in a subject in need thereof, the method comprising: co-administering an effective amount of fendiline and an effective amount of a tivantinib to the subject in need thereof.

2. The method of claim 1, wherein the effective amount of fendiline ranges from about 0.1 to 100 mg/kg of body weight.

3. The method of claim 1, wherein the effective amount of tivantinib ranges from 0.1 to 100 mg/kg of body weight.

4. The method of claim 1, wherein the tivantinib is simultaneously co-administered with fendiline during the step of co-administering.

5. The method of claim 1, wherein the tivantinib is sequentially co-administered with fendiline during the step of co-administering.

6. The method of claim 1, wherein the effective amount of fendiline ranges from about 0.1 to 100 mg/kg of body weight and wherein the effective amount of tivantinib ranges from about 0.1 to 100 mg/kg of body weight.

* * * * *